US012685749B2

(12) United States Patent
Lyngstadaas et al.

(10) Patent No.: US 12,685,749 B2
(45) **Date of Patent: *Jul. 21, 2026**

(54) MULTI-FUNCTIONAL CLEANING AND/OR DEBRIDEMENT COMPOSITION

(71) Applicant: CORTICALIS AS, Oslo (NO)

(72) Inventors: Ståle Petter Lyngstadaas, Nesoddtangen (NO); Håvard J. Haugen, Oslo (NO)

(73) Assignee: CORTICALIS AS, Oslo (NO)

( * ) Notice: Subject to any disclaimer, the term of this patent is extended or adjusted under 35 U.S.C. 154(b) by 848 days.

This patent is subject to a terminal disclaimer.

(21) Appl. No.: 17/939,670

(22) Filed: Sep. 7, 2022

(65) Prior Publication Data

US 2023/0056514 A1 Feb. 23, 2023

Related U.S. Application Data

(63) Continuation of application No. PCT/EP2021/057021, filed on Mar. 18, 2021.

(51) Int. Cl.

| | |
|---|---|
| ***A61K 33/40*** | (2006.01) |
| ***A61K 9/06*** | (2006.01) |
| ***A61K 47/12*** | (2006.01) |
| ***A61P 31/04*** | (2006.01) |

(52) U.S. Cl.

CPC ................ *A61K 33/40* (2013.01); *A61K 9/06* (2013.01); *A61K 47/12* (2013.01); *A61P 31/04* (2018.01)

(58) Field of Classification Search

CPC .......... A61K 33/40; A61K 9/06; A61K 47/12; A61P 31/04

See application file for complete search history.

(56) References Cited

U.S. PATENT DOCUMENTS

| | | |
|---|---|---|
| 4,839,156 A | 6/1989 | Ng et al. |
| 6,345,406 B1 | 2/2002 | Dodd |

(Continued)

FOREIGN PATENT DOCUMENTS

| | | |
|---|---|---|
| CN | 1292679 A | 4/2001 |
| CN | 1582139 A | 2/2005 |
| CN | 1933800 A | 3/2007 |

(Continued)

OTHER PUBLICATIONS

International Search Report and Written Opinion for PCT Patent App. No. PCT/EP2021/057021 (May 21, 2021).

(Continued)

*Primary Examiner* — Isis A Ghali
*Assistant Examiner* — Ayaan A Alam
(74) *Attorney, Agent, or Firm* — Cermak & McGowan LLP; Malcolm K. McGowan

(57) ABSTRACT

The present invention relates to a new multifunctional debridement and/or antifouling composition comprising $H_2O_2$ at a final concentration of between 0.1-5% v/v, and a composite hydrogel formulation comprising poloxamers at a concentration of 10-40% w/v, wherein the composition is in liquid form at room temperature. The composition disclosed herein is antimicrobial and/or anti-inflammatory and is particular useful in periimplantitis treatment and implant health maintenance, in periodontitis and periodontal health and in wound care and chronic ulcer care.

7 Claims, 2 Drawing Sheets

(56) References Cited

U.S. PATENT DOCUMENTS

| | | | | |
|---|---|---|---|---|
| 2004/0234923 | A1 | 11/2004 | Larsen et al. | |
| 2020/0222537 | A1 * | 7/2020 | Loupis | A61K 8/498 |

FOREIGN PATENT DOCUMENTS

| | | | | |
|---|---|---|---|---|
| EP | 2512402 | B1 * | 3/2015 | A61Q 11/00 |
| JP | 49-86275 | A | 8/1974 | |
| JP | 2008-519772 | A | 6/2008 | |
| JP | 2017-536471 | A | 12/2017 | |
| WO | WO99/47108 | A1 | 9/1999 | |
| WO | WO2003/037276 | A1 | 5/2003 | |
| WO | WO2005/072692 | A1 | 8/2005 | |
| WO | WO2006/073559 | A1 | 7/2006 | |
| WO | WO2009/083281 | A1 | 7/2009 | |
| WO | WO2011/073194 | A2 | 6/2011 | |
| WO | WO2016/081714 | A1 | 5/2016 | |
| WO | WO2016/205892 | A1 | 12/2016 | |

OTHER PUBLICATIONS

Aagren, M. D., "An Amorphous Hydrogel Enhances Epithelialisation of Wound," Acta Demato—Venereologica 1998'78:119-122.

Extended European Search Report for European Patent App. No. 20164045.4 (Sep. 9, 2020).

Chinese Office Action for a Patent Application No. 202180034972.0 (dated Nov. 24, 2023, received on Dec. 28, 2023).

Office Action from Japanese Patent App. No. 2022-554497 (Oct. 29, 2024) with English language translation thereof.

* cited by examiner

MULTI-FUNCTIONAL CLEANING AND/OR DEBRIDEMENT COMPOSITION

CROSS-REFERENCE TO RELATED APPLICATIONS

This application is a national stage entry under 35 USC 371 of PCT/EP2021/057021, filed 18 Mar. 2021, which claims priority from European application EP20164045.4, filed 18 Mar. 2020. The contents of these priority applications are incorporated herein by reference in their entirety.

TECHNICAL FIELD

The present invention relates to a new multifunctional debridement and/or antifouling composition comprising $H_2O_2$ at a final concentration of between 0.1-5% v/v, and a composite hydrogel formulation comprising Pluronic® acid poloxamers at a concentration of 10-40% w/v, wherein the composition is in liquid form at room temperature, such as at a temperature of at the most 30° C. The composition disclosed herein is antimicrobial and/or anti-inflammatory and is particular useful in periimplantitis treatment and implant health maintenance, in periodontitis and periodontal health and in wound care and chronic ulcer care.

The present invention further relates to the use of a composition according to the present invention for cleaning and/or debriding a biological surface and/or a biomaterial surface, such as in particular an implant in situ and/or a surface in the oral cavity. The composition according to the present invention can be used together with an implant cleaning and/or debridement tool, e.g. a brush, burr or a curette.

In one embodiment, the composition according to the present invention is provided in a kit, wherein the at least two components, $H_2O_2$ and poloxamers, are optionally kept separate and mixed instantly at the concomitant and/or simultaneous application.

BACKGROUND

Biological surface and/or biomaterial surfaces in situ are prone to fouling, i.e. the build-up of biofilms and necrotic tissue, as they are in constant contact with and frequently colonized by a plethora of microorganisms. They therefore require periodical cleaning and debridement with compositions that are antibacterial and anti-inflammatory without causing harm to the surrounding biological tissue in the patient and without causing microbial resistance.

Biofilms

Biofilms are structured communities of microorganisms that can be firmly attached to a surface and enmeshed in a self-produced three-dimensional (3D) extracellular matrix. Biofilms can form on, or in, living or non-living surfaces and can exist in natural and industrial settings.

Biofilms can be formed on the surface or within implanted medical tubing and medical devices, as well as on the surface and within the human body, e.g. on mucosal surfaces, or on surfaces of other bodily orifices, or in open wounds, which can lead to infections in patients. The inflammatory responses to this in turn leads to the build-up of necrotic tissue, which in turn leads to follow-up inflammatory responses of the body. In particular, biofilms can develop within the oral cavity and often results in oral diseases such as dental caries or periodontitis, gingivitis or peri-implantitis. The extracellular matrices of such biofilms contain polymeric substances, such as exopolysaccharides (EPS). The matrix produced by microorganisms can provide an essential scaffold for biofilm assembly. Additionally, it can promote microbial adhesion and cohesion while hindering diffusion, thereby making biofilms extremely difficult to treat or remove from surfaces.

The extracellular matrix contributes to the difficulty in the elimination of microbial biofilms within the oral cavity and human body, as well as on biomaterials, e.g., implants and medical devices, by antibodies, antibiotics and immune cells, which are largely unable to penetrate the dense extracellular matrix to kill the embedded microorganisms.

Biofilms on biological surfaces as well as on implants can be removed by chemical and/or mechanical cleaning and/or debridement.

Debridement

Debridement is the medical removal of a patient's dead, damaged and/or infected tissue to improve the healing potential of the remaining healthy tissue. Debridement removal may be surgical, mechanical, chemical, autolytic (self-digestion), and by maggot therapy, wherein certain species of live maggots selectively eat only necrotic tissue.

Still, the mechanical cleaning and/or debridement of a surface, is not enough as it is not able to provide any secondary chemical and/or biological cleaning/decontamination effect, thus e.g. leaving the surface open for immediate repopulation of microbes, or even leaving traces of the prior microbial populations, e.g. on the inaccessible areas of rough surfaces.

Thus, there are several antimicrobial and/or anti-inflammatory agents used in anti-fouling treatments today.

Hydrogen Peroxide

Hydrogen peroxide ($H_2O_2$) is a very pale blue liquid which appears colourless in a dilute solution, slightly more viscous than water. It is a weak acid. It has strong oxidizing properties and is therefore a powerful bleaching agent that is mostly used for bleaching paper but has also found use as a disinfectant and as an oxidizer. Hydrogen peroxide in the form of carbamide peroxide is widely used for tooth whitening (bleaching), both in professionally- and in self-administered products.

Hydrogen peroxide is unstable and slowly decomposes in the presence of light. Because of its instability, hydrogen peroxide is typically stored with a stabilizer in a weakly acidic solution in a dark coloured bottle.

Hydrogen peroxide may be used for the sterilization of various surfaces, including surgical tools and may be deployed as a vapour (VHP) for room sterilization. $H_2O_2$ demonstrates broad-spectrum efficacy against virus, microbes including but not limited to bacteria, yeasts, and bacterial spores. In general, greater activity is seen against Gram-positive than Gram-negative bacteria though; however, the presence of catalase or other peroxidases in these organisms may increase tolerance in the presence of lower concentrations. Higher concentrations of $H_2O_2$ (10 to 30% v/v) and longer contact times are required for sporicidal activity.

Hydrogen peroxide is seen as an environmentally safe alternative to chlorine-based bleaches, as it degrades to form oxygen and water and it is generally recognized as safe as an antimicrobial agent by the U.S. Food and Drug Administration (FDA).

Historically, hydrogen peroxide was used for disinfecting wounds. Today, it is thought to inhibit healing and to induce scarring, because it destroys newly formed skin cells at high concentrations. One study found that only very low concentrations (0.03% v/v solution, this is a dilution of typical 3% v/v Peroxide by 100 times) may induce healing, and only if not applied repeatedly. A 0.5% v/v solution was found to impede healing.

Pluronic® Acid

Pluronics® or poloxamers are tri-block copolymers of poly(ethylene oxide) poly(propylene oxide)-poly(ethylene oxide) (PEO-PPO-PEO). This group of synthetic polymers is thermo-reversible in aqueous solutions. The sol-gel transition is governed by the composition, molecular weight, and concentration of each constituent block polymer. The hydrophilic ethylene oxide and the hydrophobic propylene oxide give poloxamers an amphiphilic structure—meaning it has a polar, water-soluble group attached to a nonpolar water-insoluble hydrocarbon chain. Amphiphilic block copolymer molecules self-assemble into micelles (a packed chain of molecules) in aqueous solution. Micelle formation is temperature dependent and affects the degradation properties of the biomaterial: below a certain characteristic temperature known as the critical micelle temperature, both the ethylene and propylene oxide blocks are hydrated and the PPO block becomes soluble.

Poloxamers can be found either as liquids, pastes or solids. Due to their amphiphilic characteristics (presence of hydrophobic and hydrophilic components), poloxamers possess surfactant properties which allow them to interact with hydrophobic surfaces and biological membranes. Being amphiphilic also results in the ability of the individual block copolymers, known as unimers, to combine and form micelles in aqueous solutions. When the concentration of the block copolymers is below that of the critical micelle concentration (CMC), the unimers remain as molecular solutions in water. However, as the block copolymer concentration is increased above the CMC, the unimers will self-assemble and form micelles, which can take on spherical, rod-shaped or lamellar geometries. Their shapes depend on the length and concentration of the block copolymers (i.e. EO and PO), and the temperature. Micelles usually have a hydrophobic core, in this case the PO chains, and a hydrophilic shell, the EO chains.

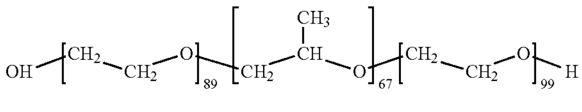

Pluronic® F-127

Pluronic® F-127, also known as Poloxamer 407, is often used in tissue engineering because of the commercial availability of a consistent product that will undergo a sol-gel transition near physiological temperature and pH. A disadvantage of Pluronic® F-127 is its fast degradation rate in vivo. To overcome this problem, Pluronic® F-127 is frequently crosslinked with another α-hydroxy or amino acid in order to alter the chemical structure of its depsipeptide unit.

Poloxamers form thermo-sensitive hydrogels, which are typically stabilized by addition of high-molecular-weight acids, such as hyaluronic acid.

Studies have documented the positive effects of poloxamer formulations in reducing inflammation, protect tissues against damage and hinder microbial adhesion. Furthermore, it is EMA and FDA approved, completely biocompatible and safe to use clinically with no known harmful effects in human cells.

Still, it is hard to apply as a cleaning and debridement agent because it will automatically form a stable gel at over 18° C., or even between temperatures of 12-20° C. (see FIG. 1) dependent of its concentration, which makes it unsuitable to use in small passages and/or for use on rough surfaces and does not lend it to application with a syringe.

Consequently, there is still sought for a means for cleaning and/or debriding fouled biological surface and/or a biomaterial surface in situ, or a means for preventing fouling of said biological surface and/or a biomaterial surface in situ by cleaning and/or sterilizing said surfaces e.g. in the oral cavity. The present invention for the first time presents such a means for effectively cleaning and/or debriding even difficult to access areas and/or rough hard surfaces such as in the oral cavity.

SUMMARY

The present invention relates to a novel antimicrobial and/or anti-inflammatory composition for cleaning and/or debriding a biological surface and/or a biomaterial surface in situ, comprising at least two components a. $H_2O_2$ at a final concentration of between 0.1-5% v/v, and b. a composite hydrogel formulation comprising poloxamers at a concentration of 10-40% w/v, wherein the composition is liquid at room temperature, such as at a temperature of at the most 30° C., such as at a temperature between 20-30° C., such as at 25° C.

The presently disclosed composition is characterized in that it comprises components a. and b. in such a ratio that the composition is in a liquid state in room temperature instead of in a gel-state.

In one embodiment of an antimicrobial and/or anti-inflammatory composition according to the present invention, the composite hydrogel formulation of component b. comprises poloxamers at a concentration of 10-40% w/v, such as at a concentration of at least 10% w/v, such as of 10, 15, 20, 25, 30, 35 or 40% w/v.

In another embodiment of an antimicrobial and/or anti-inflammatory composition according to the present invention, the composite hydrogel formulation of component b. comprises poloxamers at a concentration of at the most 40% w/v, such as of at the most 15, 20, 25, 30 or 35% w/v.

An antimicrobial and/or anti-inflammatory composition according to the present invention can be a composition wherein the $H_2O_2$ of component a. has a final concentration of 0.1-5% v/v, such as 0.5-3.0% v/v.

An antimicrobial and/or anti-inflammatory composition according to the present invention can further comprise water and/or physiological saline.

The two components of the antimicrobial and/or anti-inflammatory composition according to the present invention can be in one solution or the at least two components can be kept separate from each other until they are simultaneously mixed and applied to a biological surface and/or a biomaterial surface in situ.

In an antimicrobial and/or anti-inflammatory composition according to the present invention, wherein the components are kept separate from each other before application, the separate component a. can be a composition that comprises $H_2O_2$ at a concentration of at least 10-50% v/v.

A composition according to the present invention can further comprise microparticles having a mean particle diameter (D50) of 20-200 μm. Said microparticles are typically in a concentration between about 0.5-1000 g/L, such as between about 0.5-300 g/L. Said microparticles can be organic, or inorganic.

Inorganic microparticles comprised in a composition according to the present invention can be selected from metallic compounds.

In another aspect, said microparticles are polymer particles, mineral particles and/or metal particles.

In one aspect, said microparticles comprised in a composition according to the present invention are biodegradable, such as selected from the group consisting of bare zinc, iron, silicon, magnesium, manganese, silver and palladium.

In one aspect, a composition according to the present invention further comprises microparticles that are releasing one the following ions $Ca2+$, $F-$, $Sr2+$, $Mg2+$, or which are microparticles comprising a calcium salt compound powder, a calcium oxide compound powder, a calcium ion source and/or a calcium phosphate compound powder.

In yet another aspect, a composition according to the present invention comprises a fluoride ion source.

A composition according to the present invention can further comprise at least one mesh-forming and/or scaffolding component, which improves physical strength and/or chemical longevity of the composition after application.

Alternatively, or in addition, a composition according to the present invention can comprise a bioactive substance.

What is more, a composition according to the present invention can also comprise a further antimicrobial substance and/or debridement components.

A composition according to the present invention in one aspect has a shelf-life of at least 1 years in RT.

The present invention also relates to a kit comprising a composition according to the present invention, comprising at least two containers comprising said separated components a. and b., respectively, a syringe and a vial, a connector device, an applicator tip and an instruction leaflet and optionally a mixing device and a debridement tool, such as but not limited to a brush. Said kit can provide the two components a. and b. in a two-chamber syringe, in which case the kit further can comprise an instruction leaflet, a mixing device, an applicator tip and a debridement tool, such as a brush.

An antimicrobial and/or anti-inflammatory composition according to the present invention is intended for use in debriding and/or cleaning a biological surface and/or a biomaterial surface in situ, e.g. use in removal of biofouling, biofilm and/or necrotic tissue from such a biological surface and/or a biomaterial surface in situ.

An antimicrobial and/or anti-inflammatory composition according to the present invention can typically be employed for use in the treatment and/or prevention of periimplantitis, gingivitis and/or mucositis, peri-implant mucositis and/or periodontitis.

In consequence, the present invention relates to a method for treating and/or preventing periimplantitis, gingivitis and/or mucositis, peri-implant mucositis and/or periodontitis, comprising cleaning and/or debriding a biological surface and/or a biomaterial surface in situ by applying a composition according to the present invention to said fouled, biofilmed and/or necrotized surface.

DEFINITIONS and ABBREVIATIONS

The term "microparticle" is herein meant to describe a particle having a mean particle diameter (D50) between about 1 and 1000 μm. Typically, in the present invention, a microparticle is used that has a mean particle diameter (D50) between 20-200 μm.

The present invention provides the means to clean and/or debride a medical and/or dental implant. In the present context, the term "implant" typically means a medical and/or dental implant.

In the present context, the term "dental implant" includes within its scope any device intended to be implanted into the oral cavity of a vertebrate animal, in particular a mammal such as a human, for example in tooth restoration procedures. Dental implants are herein selected from the group consisting of: Implants, bars, bridges, abutments, crowns, caps, and prosthetic parts in the oral cavity. Dental implants may also be denoted as dental prosthetic devices. Generally, a dental implant is composed of one or several implant parts. For instance, a dental implant usually comprises a dental fixture coupled to secondary implant parts, such as an abutment and/or a dental restoration such as a crown, bridge or denture. However, any device, such as a dental fixture, intended for implantation may alone be referred to as an implant even if other parts are to be connected thereto.

In the present context, the term "orthopaedic implant" includes within its scope any device intended to be implanted into the body of a vertebrate animal, in particular a mammal such as a human, for preservation and restoration of the function of the musculoskeletal system, particularly joints and bones, including the alleviation of pain in these structures. Non-limiting examples of orthopaedic implants are hip-joint prostheses, knee prostheses, elbow prostheses, finger prostheses, cochlear prostheses, and fixation screws.

In the present context, the term "vascular stent" refers to a tubular implant arranged for insertion into blood vessels of a vertebrate animal, in particular a mammal such as a human, in order to prevent or counteract a localized flow constriction, i.e. in order to counteract significant decreases in blood vessel diameter.

Hard tissues are, for example, bone, cementum, dentin, enamel, teeth, roots, cartilage and ligaments. Soft tissues are for example tissues that connect, support, or surround other structures and organs of the body, not being hard tissue such as bone. Soft tissue includes tendons, ligaments, fascia, skin, fibrous tissues, fat, and synovial membranes, muscles, nerves and blood vessels.

The term "debridement" in the present context means cleaning of a tissue surface, such as a surgically exposed hard and/or soft tissue surface, in order to remove, for example, biofilm, concrements, microbes, unwanted tissue, cells and cell residues, scar tissue, and/or necrotic tissue. Debridement may, for example, be performed in order to control and/or treat local infections, inflammations, foreign body reactions, pathological conditions, and/or regenerative processes (e.g. periodontitis, periimplantitis).

As used herein, a "biofilm" includes an extracellular matrix and one or more microorganisms such as, but not limited to, bacteria, fungi, algae and protozoa, which is attached to a surface. For example, but not by way of limitation, such surfaces can include tooth, mucosal, apatitic, bone and abiotic (e.g., implant, dentures, pipes, etc.) surfaces.

In the present context, the term "peroxide" is used interchangeably with Hydrogen peroxide ($H_2O_2$).

A microorganism, or microbe, is a microscopic organism, which may exist in its single-celled form or in a colony of cells. Microorganisms include all unicellular organisms and so are extremely diverse. All of the Archaea and Bacteria are microorganisms (Prokaryotes). Some protists are related to animals and some to green plants. Many of the multicellular organisms are microscopic, namely micro-animals, some fungi and some algae.

An antimicrobial is an agent that kills microorganisms or stops their growth. Antimicrobial medicines can be grouped according to the microorganisms they act primarily against. For example, antibiotics are used against bacteria, and antifungals are used against fungi. They can also be classified according to their function. Agents that kill microbes are microbicidal, while those that merely inhibit their growth are called biostatic both are included in the term"antimicrobial". The use of antimicrobial medicines to treat infection is known as antimicrobial chemotherapy, while the use of antimicrobial medicines to prevent infection is known as antimicrobial prophylaxis.

A virus is a small infectious agent that replicates only inside the living cells of an organism. Viruses can infect all types of life forms, from animals and plants to microorganisms, including bacteria and archaea.

Antiviral drugs are a class of medication used specifically for treating viral infections rather than bacterial ones. Most antivirals are used for specific viral infections, while a broad-spectrum antiviral is effective against a wide range of viruses. Unlike most antibiotics, antiviral drugs do not destroy their target pathogen; instead they inhibit their development.

Antiviral drugs are one class of antimicrobials, a larger group which also includes antibiotic (also termed antibacterial), antifungal and antiparasitic drugs, or antiviral drugs based on monoclonal antibodies. Most antivirals are considered relatively harmless to the host, and therefore can be used to treat infections. They should be distinguished from viricides, which are not medication but deactivate or destroy virus particles, either inside or outside the body. Natural antivirals are produced by some plants such as eucalyptus and Australian tea trees.

As used in the present context, the term "antimicrobial", means that the composition is effective against microbes and virus. In its broadest meaning, the composition of the present invention is antimicrobial, i.e. it is antibacterial, antiviral, a bactericide and/or a viricide.

As used herein, the term "about" or "approximately" means within an acceptable error range for the particular value as determined by one of ordinary skill in the art, which will depend in part on how the value is measured or determined, i.e., the limitations of the measurement system.

Figure 1A:
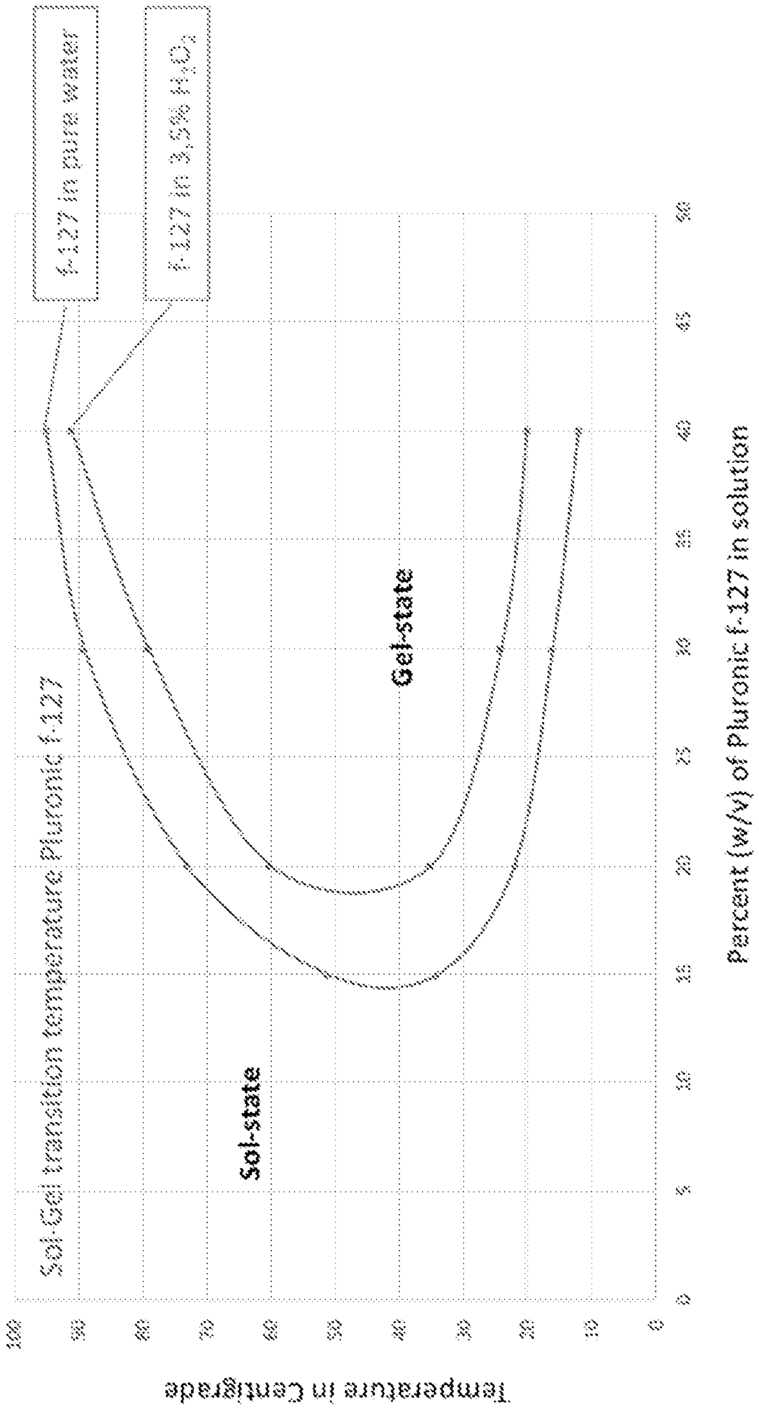
FIG. 1: 1A: Sol-Gel transition temperature for Pluronic® f-127 in $H_2O_2$ at a concentration of 3,5% v/v (lower graph) compared to Sol-Gel transition temperature for Pluronic® f-127 in pure water (upper graph).
Figure 1B:
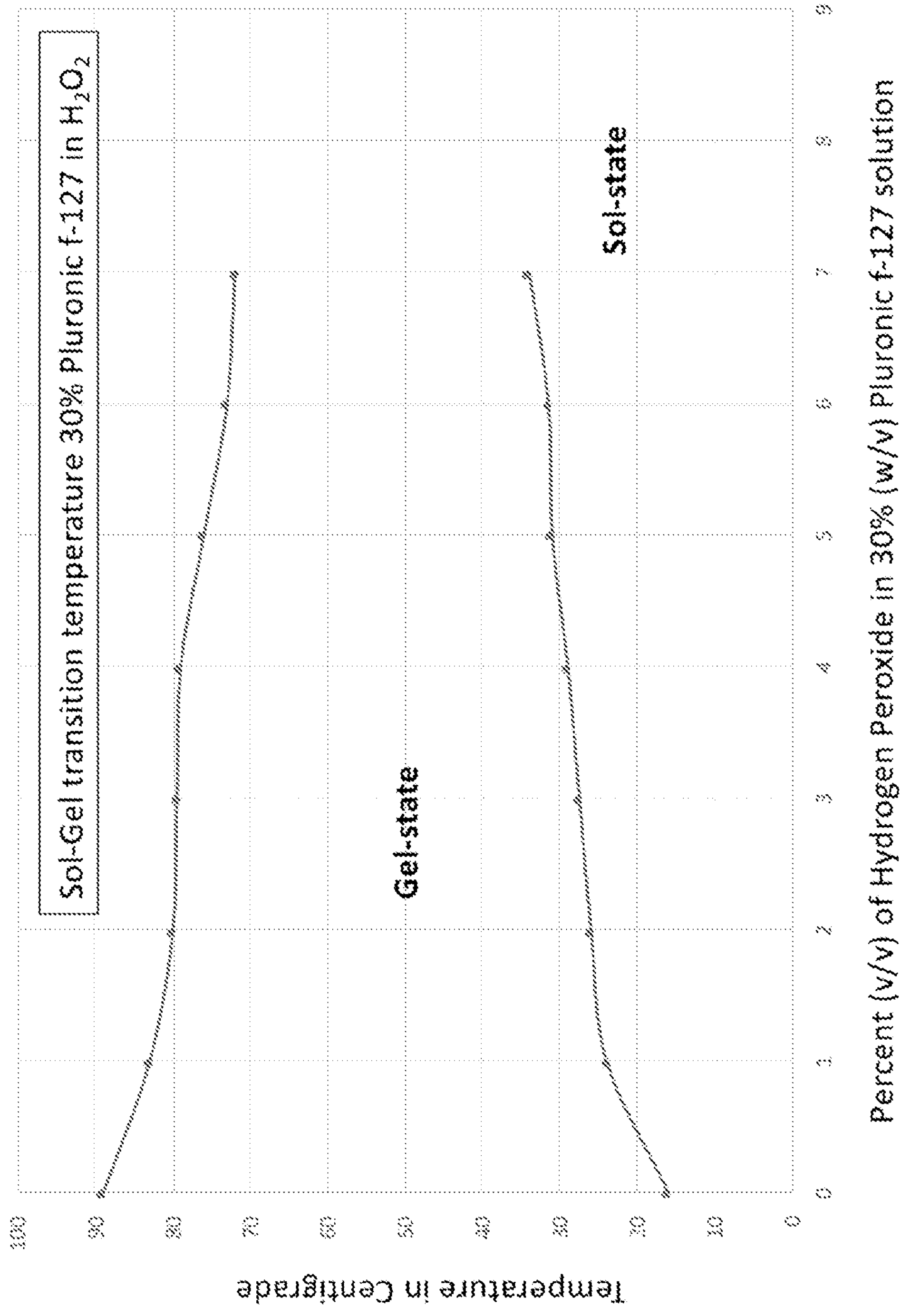

1B: Sol-Gel transition in relation to % $H_2O_2$ for Pluronic® f-127 (30% w/v) in Hydrogen Peroxide in different concentrations (v/v).

DETAILED DESCRIPTION

The presently described composition is a long sought for means for effectively cleaning and/or debriding a biological surface and/or a biomaterial surface in situ. E.g., but not limited to a surface in the oral cavity for rapid and effective treatment without damaging the to be cleaned surface structure, and essentially without leaving contaminating material residues, at the same time displaying an antimicrobial and/or anti-inflammatory effect.

The presently described composition is a water soluble and easy to rinse off, tissue-friendly non-ionic surfactant. It comprises a non-toxic formulation of well-studied active ingredients in clinical use which is particularly suitable for injectable, oral and cutaneous applications. The herein for the first time described compositions is proven to be non-sensitizing and non-irritating in clinical tests. The composition of the invention is compatible with other therapeutic agents against biofouling and inflammation.

The composition described herein has a liquid state at room temperature that makes for trouble-free mixing and application. At temperatures of no more than 30° Celsius, such as at RT, it displays an easy flowing liquid consistence with surfactant effect that that allows the compositions to reach difficult places when applied into narrow defects. When applied, the patient's natural body temperature initiates micelles to link and to quickly form a stable gel at body temperature, allowing prolonged and intimate contact with implant surfaces and tissue at the application site.

The presently described composition can further be formulated to contain bio-resorbable micro-particles to assist in the mechanical debridement of micro-rough implant surfaces. Which will facilitate a clean surface with intact original structure. The gel-particle suspension can be used with debridement tools, such as brushes (e.g. TiBrush®), or other cleaning devices.

The composition of the present invention mimics the natural release of reactive oxygen species (ROS) from peroxide produced by human cells. The charge from the reactive oxygen destroys microbial membranes and the oxygen itself is also toxic to anaerobic bacteria. The human cells themselves are protected against ROS by enzymes in their cell membrane and the local tissue can benefit from the increase in oxygen. Microbes have no such protection, nor can they develop resistance because of fundamental differences in their cell-membrane design. Thus the composition can effectively dissolve biofilm, debris and mineral deposit as well as dissolve extracellular organics at the application site.

Moreover, the acidity of the peroxide helps cells dissolve mineral deposits as well as to break down and remove extracellular organics and calcifications from the contaminated implant.

Cells use peroxide as a second messenger system that activate cellular defence against microbes. The presently disclosed composition mimics this signal to stimulate and strengthen the local cellular defence network.

Through the active oxygen released from the hydrogel, the use of the herein presented composition also removes carbon contamination from a titanium containing implant surface and reactivates the titanium dioxide layer of the implant. This process re-establishes the original charge and hydrophilicity of the implant, restoring the optimal biological surface properties. This is a major factor for further survival, or even successful reintegration, of said treated implant. The effect is visualized in the experimental section by improved cell spreading and super-hydrophilicity.

The present composition is an advanced micelle forming gel formulation that works in synergy with natural occurring oxygen to break down and remove biofouling, eliminate microbes, keep tissue and implant moist and to reactivate the titanium implant surfaces The hydrogel component of the composition and the active oxygen work in synergy to avoid foaming and keeps oxygen in place at the surface for a prolonged biological and chemical effect. The use of the composition provides moisture and allows the charged oxygen to work without risk of drying out tissue and/or implant, during which the active oxygen eradicates microbes that are then suspended and entrapped in the gel that has formed in the body temperature. Organic contaminants are in turn denatured by the strong detergent effect, broken down by the active oxygen and dissolved and entrapped in the gel. Both gel and oxygen reduce inflammation and support tissue health. The gel formed in the body temperature allows for prolonged local effect of active oxygen that in turn strengthens the cellular defence network. In synergy, the gel and the active oxygen both removes contaminants and reactivates an implant surface. The inversed thermodynamics of the gel work with the disruptive effect of active oxygen to form an equilibrium between micelle-sol-state and gel-state that increases the debridement effect significantly.

The presently described composition is a novel formula of biocompatible hydrogel with strong, non-ionic detergent properties with improved sol-gel dynamics for solubilization and entrapment of debris and microbes for effectively cleaning and/or debriding a biological surface and/or a biomaterial surface in situ. It is easy rinsed off with water, and it completely decomposes to water, oxygen and carbon oxid.

The presently disclosed composition provides a novel and improved means for the treatment and elimination of biofilms; the prevention of biofilm formation; biofilm extracellular matrix degradation; and the inhibition of bacterial viability and growth within the biofilm. In particular, the presently disclosed subject matter provides a composition for the prevention and/or treatment of an oral disease (e.g., dental caries, periodontitis, gingivitis, mucositis and/or peri-implantitis).

The invention itself is based on a combination of hydrogen peroxide ($H_2O_2$) and poloxamers in such a concentration that the composition is in a liquid form in RT, i.e. at a temperature of no more than 30° C., but due to elevation of temperature to body temperature, converts into a gel-state at the application site in situ. The $H_2O_2$ component of the composition can either be in the form of a concentrate (at a concentration of at least 10-50% v/v.) in a separate vial for mixing immediately before use in on embodiment applied with a mixing connector typically of Luer-lock design), or provided as dissolved directly into a hydrogel consisting of poloxamers and water (or physiological saline) with a typical final concentration of 0.5-5%. The poloxamer component itself can be any of the poloxamers, e.g. the F-127 variety. The concentration of poloxamers is typically 0.1-10% w/v, such as 0.1-2.5% w/v.

Poloxamers work both as solubilizer and detergent in the composition disclosed herein, as well as moisturizers and dynamic viscosity modifiers. The hydrogel formulation forms a sticky gel when heated to body temperature by self-organizing micelles of poloxamers into a packed structure. This make the gel stay at the application site and exert its activity where it is needed. This hydrogel activity is further improved by adding charged oxygen that dissolves the packed micelle structure, thus establishing a dynamic equilibrium between sol-state and gel-state. This dynamic state facilitates efficient solubilization and entrapment of particles, microbes and pollutants during the debridement procedure.

The present innovation is based on a synergetic effect between poloxamers and peroxide. Poloxamers have a reversed thermodynamic ability to form a "packed" micelle structure with several micelles combining to form a hydrogel. This ability increases with increasing temperature and is shifted toward the gel state at physiological conditions (such as at >20 degrees Celsius). This sol-gel transition forms a stable gel on e.g. living skin, mucosa, wounds for prolonged function as moisture and/or as wound dressing that can to some extent absorb organic contaminants.

However, when mixed with hydrogen peroxide the present invention for the first time discloses that the sol-gel transition is more dynamic and less stable, so that the transition between sol-state (single solubilized micelles) and gel-state (packed micelle structure) is in a "dynamic" equilibrium with the peroxide radical activity even under physiological conditions (=high temperature). In effect this means that in the presence of peroxide, the packed micelle structure is dissolved and reforms constantly (not only by lowering or increasing temperature) also when the gel is applied onto human tissue/skin/mucosa. This effect increases the detergent and entrapment effect of the poloxamers significantly.

Combined with the effect of hydrogen peroxide to release free oxygen radicals on viral particles, microbes and necrotic tissue, the sol-gel transitions dissolve and entrap organic contamination that are then removed when the gel is washed off.

Another advantage of the present composition is that the addition of hydrogen peroxide to the poloxamers increases the temperature at when the packed micelle structure forms. I.e. that the poloxamer gel, containing low concentrations of peroxide, is liquid at room temperature and thus can be applied through a syringe needle or from a dispenser bottle without clogging of the nozzle. This is not possible with poloxamers alone because it starts forming a stable "packed micelle" gel already at room temperature and thus is very hard to squeeze through a narrow tip of a syringe, or a pump applicator from a dispenser bottle. Poloxamer for wound care is therefore sold as gel in a box or a tube.

The increased effect from the combination of weak peroxide and poloxamers was unforeseen and surprising.

The decreased viscosity of the poloxamer hydrogel in combination with peroxide also assists during application. It enables the cleaning and/or debridement composition to reach narrow spaces and undercuts that a poloxamer gel alone cannot get into because of its gel-state nature at physiological temperature. Thus, it is more efficient in cleaning rough (implant) surfaces, narrow spaces such as between bone and implant/tooth and in wrinkles on skin.

Compositions

The present invention relates to a novel antimicrobial and/or anti-inflammatory composition for cleaning and/or debriding a biological surface and/or a biomaterial surface in situ, comprising at least two components a. $H_2O_2$ at a final concentration of between 0.1-5 v/v, and
b. a composite hydrogel formulation comprising poloxamers at a concentration of 10-40% w/v, and wherein the composition is liquid at room temperature, such as at a temperature of at the most 30° C., such as at a temperature between 20-30° C., such as at 25° C.

The presently disclosed composition is characterized in that it comprises components a. and b. in such a ratio that the composition is in a liquid state in room temperature instead of in a gel-state. Typical ratios of concentrations between component a. and component b. are approximately 1:10 (concentration of $H_2O_2$: concentration of poloxamers). In general, the higher the concentration of the poloxamers, the higher the concentration of the $H_2O_2$ is needed to keep the composition in a liquid state (Sol-state) at temperatures of between 20-30° C. Exemplary concentration ratios can e.g. be >2.0% v/v $H_202$:15% w/v poloxamers, >2.5% v/v $H_202$: 20% w/v poloxamers, >3% v/v $H_202$:25% w/v poloxamers, >3.5% v/v $H_202$:30% w/v poloxamers, >5% v/v $H_202$:40% w/v poloxamers.

In one embodiment of an antimicrobial and/or anti-inflammatory composition according to the present invention, the composite hydrogel formulation of component b. comprises poloxamers at a concentration of 10-40% w/v, such as at a concentration of at least 10% w/v, such as of 10, 15, 20, 25, 30, 35 or 40% w/v.

In another embodiment of an antimicrobial and/or anti-inflammatory composition according to the present invention, the composite hydrogel formulation of component b. comprises poloxamers at a concentration of at the most 40% w/v, such as of at the most 15, 20, 25, 30 or 35% w/v.

An antimicrobial and/or anti-inflammatory composition according to the present invention can be a composition wherein the $H_2O_2$ of component a. has a final concentration of 0.1-5% v/v, such as 0.5-3% v/v, such as 0.1-5% v/v. In one embodiment, the $H_2O_2$ of component a. has a final concentration of no more than 5% v/v, such as 0.1-5% v/v, such as 1, 2, 3, 4 or 5% v/v.

An antimicrobial and/or anti-inflammatory composition according to the present invention can further comprise water and/or physiological saline.

The two components of the antimicrobial and/or anti-inflammatory composition according to the present invention can be in one solution or the at least two components can be kept separate from each other until they are simultaneously mixed and applied to a biological surface and/or a biomaterial surface in situ.

In an antimicrobial and/or anti-inflammatory composition according to the present invention, wherein the components are kept separate from each other before application, the separate component a. can be a composition that comprises $H_2O_2$ at a concentration of at least 10-50% v/v, such as at the most 10, 20, 30, 40 or 50% v/v. In one embodiment, a composition of the present invention comprises $H_2O_2$ at a concentration of 30% v/v.

Emulsifier(s) and/or Viscosity Modifier(s)

In one embodiment, the antimicrobial and/or anti-inflammatory composition according to the present invention further comprises one or more emulsifier(s) and/or viscosity modifier(s). Said emulsifier and/or viscosity modifier may be selected from the group consisting of glycerine, glycols, polyethylene glycols (PEG), polyoxyethylene polyoxypropylene block copolymer (poloxamer polyols), polyglycol alginate (PGA), CMC (carboxyl methyl cellulose), glycerol, Aloe Vera gel, alginate, hyaluronic acid (HA) and citosan.

The antimicrobial and/or anti-inflammatory composition according to the present invention may also comprise one or more detergent(s) selected from the group consisting of SDS (sodium dodecyl sulfate), sodium stannate, sodium pyrophosphate, oxine and SLS (sodium lauryl sulfate).

The antimicrobial and/or anti-inflammatory composition according to the invention may further comprise one or more flavouring oil(s), such as, but not limited to oils of spearmint, peppermint, wintergreen, sassafras, clove, sage, eucalyptus, marjoram, cinnamon and methyl salicylate and menthol.

The antimicrobial and/or anti-inflammatory composition according to the invention may further comprise one or more weak acidic buffers.

Microparticles

A composition according to the present invention can further comprise microparticles having a mean particle diameter (D50) of 20-200 μm. Said microparticles are typically in a concentration between about 0.5-1000 g/L, such as between about 0.5-300 g/L.

A composition according to the present invention can comprise microparticles which are releasing one or more of ions selected from the group consisting of $Ca^{2+}$, $F^-$, $Sr^{2+}$ and $Mg^{2+}$.

In one aspect, a composition according to the present invention comprises microparticles consisting of calcium salt compound powder which is selected from the group consisting of calcium sulfate, calcium carbonate, calcium aluminate, calcium lactate, calcium nitrate, calcium citrate, calcium acetate, calcium stearate, calcium fumarate, calcium malate, calcium chloride, calcium bromide, calcium fluoride, calcium iodide, calcium saccharate, calcium oxalate, calcium gluconate, calcium propionate, calcium caseinate, calcium glycerophosphate, and combinations thereof.

In another aspect, a composition according to the present invention comprises microparticles consisting of calcium oxide compound powder which is selected from the group consisting of calcium oxide, calcium peroxide, calcium hydroxide, and combinations thereof.

In another aspect, a composition according to the present invention comprises microparticles providing a calcium ion source which are selected from the group consisting of calcium chloride, calcium sulfate, calcium aluminosilicate, calcium carbonate, calcium chloride, calcium ascorbate, and calcium oxide, and wherein the phosphate ion source is sodium phosphate, diphosphate.

In yet another aspect, a composition according to the present invention comprises microparticles consisting of a calcium phosphate compound powder which is selected from the group consisting of octacalcium phosphate, heptacalcium phosphate, pentacalcium phosphate, tetracalcium phosphate, tricalcium phosphate, dicalcium phosphate, monocalcium phosphate, calcium pyrophosphate, calcium metaphosphate, calcium phosphinate, amorphous calcium phosphate, calcium hydroxide phosphate and combinations thereof.

In yet another aspect, a composition according to the present invention comprises additional microparticles consisting of a compound selected from the group consisting of silica, silicate glasses, quartz, zinc oxide, barium sulfate, barium silicate, strontium silicate, barium borosilicate, strontium borosilicate, borosilicate, lithium silicate, amorphous silica, bismuth compounds, ammoniated or deammoniated calcium phosphate, alumina, zirconia, tin oxide, titania, apatites, silica glass fillers, calcium silicate based fillers, hydroxyapatites, barium sulfate, bismuth subcarbonate, Iron, Silicon magnesium, zinc, Silver, Manganese, Palladium, Radium or mixtures thereof.

In yet another aspect, a composition according to the present invention comprises microparticles being polymer particles, mineral particles, metal particles, barium boroaluminosilicate glass, fluoroaluminosilicate glass, silica, silicate glass, quartz, barium silicate glass, strontium silicate glass, bariumboro Silicate glass, borosilicate glass, barium aluminofluorosilicate glass, lithium silicate, amorphous silica, barium magnesium aluminosilicate glass, barium aluminosilicate glass, strontium aluminum-borosilicate glass; strontium aluminofluorosilicate glass, amorphous silica, zirconium silicate glass, or mixtures thereof.

What is more, a composition according to the present invention can further include a fluoride ion source, wherein the fluoride ion source can be selected from the group consisting of Na 2 SiF 6, CaF 2, SrF 2, NaF, NaPO 3 F, NaKF 6 PO 3, K 2 SiF 6, F 6. NaP, NaSbF 6, KSbF 6, F 6 KP and mixtures thereof.

When the composition according to the present invention is intended for use in cleaning and/or debriding dental implants with a metal surface, the microparticles are preferably biocompatible and solid (hard) and may also be biodegradable.

The solid microparticles may be selected from the group of material consisting of TiO2i zirconium oxide, diamond dust (carbons), polymers, polylactic acid (beans), mineral, ceramic, dialuminium trioxide, calcium carbonate, calcium phosphate, apatite crystals, bone ceramic particles (hydroxyapatite/calcium phosphate), titanium, zirkonium, aluminium oxide, carborundum, pumice, and silica.

The choice of material for the solid microparticles is preferably made depending on which material, e.g. a metal implant or a hard tissue surface, is to be cleaned/debrided by the composition of the invention, in order to fit the roughness of the material to allow for efficient cleaning/debriding of the material while still not damaging it.

One advantage with the selection of the above specified size of the microparticles is that surface treatment of dental implants typically results in a diameter size of indents formed which is between 80-180 μm. Therefore, the presence of the solid microparticles in the composition of the invention makes the composition particularly suitable for the in situ cleaning and/or debridement of implants in the oral cavity, as the microparticles are of a size that allows their entry into the indents to clean these, while still being large enough to not cause inflammatory reactions and/or to be encapsulated by the body in fibrous capsules.

Said microparticles can be organic, or inorganic.

Organic microparticles comprised in a composition according to the present invention can be selected from the nonlimiting group consisting of crystals of amino acids, biopolymers, chitosan, alginates, poloxamers, collagen, hyaluronic acid, PEG, and organic acids (including insoluble salts thereof such as but not limited to tartar).

Inorganic microparticles comprised in a composition according to the present invention can be selected from metallic compounds, e.g. selected from the group consisting of iron, titanium, silicon magnesium, zinc, zirconium, silver, manganese, palladium, radium, calcium and barium.

In one aspect, said microparticles comprised in a composition according to the present invention are biodegradable, such as selected from the group consisting of bare zinc, iron, silicon, magnesium, manganese, silver and palladium.

An antimicrobial and/or anti-inflammatory composition according to the present invention which comprises microparticles is typically formulated as a suspension of solid particles in a liquid.

Mesh-Forming and/or Scaffolding Component

A composition according to the present invention can further comprise at least one mesh-forming and/or scaffolding component. Typically, the at least one mesh-forming and/or scaffolding component is selected from the group consisting of silk fibres, carbon fibres, silicates, borosilicates, collagens, and spider web silk, which improves physical strength and/or chemical longevity of the composition after application.

Bioactive Substance

Alternatively, or in addition, a composition according to the present invention can comprise a bioactive substance, typically selected from the group consisting of EMD, peptides, drugs, bio active ions, small molecules, radioactive molecules, antimicrobial molecules and radio-opaque molecules.

Debridement Components and Antimicrobial Substances

What is more, a composition according to the present invention can also comprise a further antimicrobial substance and/or debridement component.

In the present context, a further antimicrobial substance comprised in the composition according to the present invention can be selected from the non-exclusive list consisting of amoxicillin, doxycycline, cephalexin, ciprofloxacin, clindamycin, metronidazole, azithromycin, sulfamethoxazole and trimethoprim.

In one aspect, a further antimicrobial substance comprised in the composition according to the present invention is tetracycline, doxycycline, macrolides, penicillins (stabilized), chlorhexidine, chloramines and mixtures thereof.

In one aspect, a composition according to the present invention comprises a further anti-inflammatory substance.

Shelf-Life of at Least 1 Year at Room Temperature (RT)

A composition according to the present invention in one aspect has a shelf-life of at least 1 year at RT.

A Kit

The present invention also relates to a kit comprising a composition according to the present invention, comprising at least two containers comprising said separated components a. and b., respectively, a syringe and a vial, a connector device, an applicator tip and an instruction leaflet and optionally a mixing device and a debridement tool, such as but not limited to a brush. Said kit can provide the two components a. and b. in a two-chamber syringe, in which case the kit further can also comprise an instruction leaflet, a mixing device, an applicator tip and a debridement tool, such as but not limited to a brush.

An antimicrobial and/or anti-inflammatory composition according to the present invention can be mixed before application and eventual storage or stored separately and mixed directly or shortly before and/or at the time of application. The application therefore, in another aspect is directed to a kit comprising a first container comprising component a), a second container comprising component b), and optionally at least one more (third or fourth, etc.) container comprising a component (c), (d), (e), etc.) which can e.g. comprise microparticles and/or a mesh-forming substance and/or a bioactive substance and/or a debridement component and/or a further antimicrobial and/or anti-inflammatory substance.

Optionally such a kit may also comprise instructions for the preparation of the composition of the invention. The kit may also comprise one or more device(s) for the application of the composition to a subject. Such a device may e.g. be a syringe or an implant cleaning and/or debridement tool for cleaning and/or debriding an implant, such as in the oral cavity.

Preferably the implant cleaning and/or debridement tool comprises an elongated base member formed of at least two wires being twisted with each other, and a plurality of bristles fixed between said twisted wires and extending away from said twisted wires, whereby said bristles are positioned in a cleaning section at a first end of said base member; and that said bristles consist of titanium and/or a titanium alloy. A kit of the invention may also comprise the composition of the invention in one or more container(s) and an implant cleaning and/or debridement tool for cleaning and/or debriding an implant in the oral cavity.

One example of such an implant cleaning/debridement tool for cleaning a dental implant and/or debriding a hard tissue surface is disclosed in U.S. Pat. No. 6,345,406, another example is given in WO 2009/083281.

The implant cleaning/debridement tool disclosed in WO 2009/083281 has bristles with diameters of 0.2 mm. In one aspect of the invention, a composition of the invention is particularly suitable to be used with this tool comprising solid microparticles in the composition of a size that will allow for an efficient cleaning of an implant and/or hard surface in the oral cavity. For this aspect, the microparticles optimally have a size about 150 μm, such as between 100 and 150 μm, because the body tends to integrate particles in fibrous capsules when the particles are between 10-100 μm.

The present invention in one aspect thus relates to a kit comprising a composition according to any one of the preceding claims, comprising a. at least two containers comprising said components a. and b., respectively,
b. a syringe and a vial,
c. a connector device,
d. an applicator tip, and
e. an instruction leaflet.

In another aspect, the present invention relates to a kit further comprising f. a mixing device and
g. a debridement tool.

In a presently preferred aspect, a kit comprising a composition according to the present invention typically provides the two components a. and b. in a two-chamber syringe, further comprising an instruction leaflet, a mixing device, an applicator tip and optionally a debridement tool.

In one aspect of the present invention, the kit further comprises a bone graft material, such any commercially available bone graft material (Titanoxyd scaffold, BioOss, Emdogain, biceramics, SmartBone etc.).

Use

The presently disclosed composition is intended for use in cleaning and/or debriding a biological surface and/or a biomaterial surface in situ.

The presently disclosed composition is especially useful for application in peri-implant defects, but the formulation may be tailored to fit with various clinical procedures.

E.g. a formulation for use in treating and/or preventing periimplantitis will typically comprise a higher content of active oxygen and micro-mechanical debridement particles A typical formulation for treating and/or preventing peri-implant mucositis will comprise increased active oxygen and increased sol-gel activity.

A typical formulation for peri-implant maintenance, peri-implant prophylaxis and post-operative follow-up comprises high active oxygen concentration.

However, the presently disclosed composition can also be used for other oral procedures, such as during surgical debridement of periodontal defects, for preparation before regenerative procedures, in periodontal maintenance treatment, in periodontitis prophylaxis (dental hygienist), as well as in endodontics, both endodontally and in apical surgery.

What is more, the presently disclosed composition can further be used for cleaning and/or debriding outside the oral cavity, such as, but not limited to orthopaedic revision surgery, debridement of transdermal devices, in dermal wound care for cleaning of acute wounds and/or in debridement of chronic ulcers and burn.

An antimicrobial and/or anti-inflammatory composition according to the present invention can typically be employed for use in the treatment and/or prevention of per-implantitis, gingivitis and/or mucositis, peri-implant mucositis and/or periodontitis.

Periimplantitis is a typical complication related to oro-dental rehabilitation through the use of implants, i.e. a peri-implant disease, which is well-known to the person skilled in the art as an inflammatory reaction in which there is a loss of the bony support of the implant accompanied by inflammation. The aetiology of the disease is conditioned by the status of the tissue surrounding the implant, implant design, degree of roughness, the poor alignment of implant components, external morphology and excessive mechanical load.

The presently described antimicrobial and/or anti-inflammatory composition for the first time offers the means for an effective and rapid cleaning of an implant and/or for debriding a hard surface in the oral cavity essentially without damaging of the anatomical structure or of the implant and/or hard surface itself, and essentially without leaving contaminating material residues on the treated surface.

The invention therefore in one aspect is directed to the antimicrobial and/or anti inflammatory composition as defined herein and/or the kit for preparing the composition of the invention as defined herein, for use as a medicament.

Thus, the present invention relates to the use of an antimicrobial and/or anti-inflammatory composition according to the present invention for cleaning and/or debriding an implant in the oral cavity, such as an implant in situ, a hard surface in the oral cavity, such as an outer surface of a hard tissue in the oral cavity, a surgically exposed hard surface in the oral cavity, a wound in the oral cavity, such as a wound resulting from periimplantitis or a surgical wound, a periodontal defect and/or periodontal wound, and/or an oral hard tissue defect.

The invention also relates to the use of the antimicrobial and/or anti-inflammatory composition as defined herein and/or the kit for preparing the composition of the invention as defined herein, for the preparation of a medicament and/or a pharmaceutical and/or cosmetic composition, for cleaning and/or debriding an implant in the oral cavity, such as an implant in situ, a hard surface in the oral cavity, such as an outer surface of a hard tissue in the oral cavity, a surgically exposed hard surface in the oral cavity, a wound in the oral cavity, such as a wound resulting from periimplantitis or a surgical wound, a periodontal defect and/or periodontal wound, and/or an oral hard tissue defect.

The invention is also directed to the antimicrobial and/or anti-inflammatory composition as defined herein or the kit for preparing the composition of the invention as defined herein for use for cleaning and/or debriding an implant in the oral cavity, such as an implant in situ, a hard surface in the oral cavity, such as an outer surface of a hard tissue in the oral cavity, a surgically exposed hard surface in the oral cavity, a wound in the oral cavity, such as a wound resulting from periimplantitis or a surgical wound, a periodontal defect and/or periodontal wound, and/or an oral hard tissue defect.

Another presently preferred embodiment is directed to the use of an antimicrobial and/or anti-inflammatory composition according to the present invention together with an implant cleaning and/or debridement tool, for cleaning an implant and/or debriding a hard surface in the oral cavity. Said implant cleaning and/or debridement tool is e.g. characterized by comprising an elongated base member formed of at least two wires being twisted with each other, and a plurality of bristles fixed between said twisted wires and extending away from said twisted wires, whereby said bristles are positioned in a cleaning section at a first end of said base member; and that said bristles comprise or consist of titanium and/or a titanium alloy.

Many medical implants, such as e.g. dental implants, orthopaedic implants and vascular stents, are metallic, i.e. they are made of a metal material. The present invention consequently relates to the use of an antimicrobial and/or anti-inflammatory composition according to the present invention, alternatively together with an implant cleaning and/or debridement tool, for cleaning and/or debriding an implant made of a metal material. Examples of metal materials commonly utilized for constructing metallic medical implants are steel, titanium, zirconium, tantalum, niobium, hafnium and alloys thereof. In particular, titanium and titanium alloys have proven to be suitable to utilize for constructing medical implants.

On the other hand, both medical and dental implants can at least partially, as well as in full (full-ceramic implants) consist of porcelain and/or ceramic, such as of zirconium oxide and/or hydroxyapatite, or any other ceramic or porcelain material known to the person skilled in the art as being suitable for implantry. Thus, the present invention equally relates to the use of an antimicrobial and/or anti-inflammatory composition according to the present invention, alternatively together with an implant cleaning and/or debridement tool, for cleaning and/or debriding an implant made of, or comprising, porcelain and/or ceramic. Consequently, the present invention is also directed to the use of a composition of the invention for the preparation of a medicament and/or a pharmaceutical and/or cosmetic composition for the cleaning and/or debridement of an implant made of or comprising porcelain and/or ceramic. Also, the invention is directed to a composition of the invention alternatively for use for cleaning and/or debriding an implant made of or comprising porcelain and/or ceramic.

Dental implants are typically utilized in dental restoration procedures in patients having lost one or more of their teeth. A dental implant comprises a dental fixture, which is utilized as an artificial tooth root replacement. Thus, the dental fixture serves as a root for a new tooth. The dental fixture is typically a screw, i.e. it has the shape of a screw, and it is typically made of titanium, a titanium alloy, zirconium or a zirconium alloy. The screw is surgically implanted into the jawbone, where after the bone tissue grows around the screw and the screw is fixated in the bone with the bone in close contact with the implant surface. Once the implant screw is firmly anchored in the jawbone, it may be elongated by attachment of an abutment to the screw. The abutment may, just as the screw, be made of titanium, a titanium alloy, zirconium or a zirconium alloy. The shape and size of the utilized abutment are adjusted such that it precisely reaches up through the mucosa after attachment to the screw. A dental restoration such as a crown, bridge or denture may then be attached to the abutment. Alternatively, the implant screw has such a shape and size that it reaches up through the mucosa after implantation, whereby no abutment is needed and a dental restoration such as a crown, bridge or denture may be attached directly to the screw.

The present invention consequently relates to the use of an antimicrobial and/or anti-inflammatory composition according to the present invention, alternatively together with an implant cleaning and/or debridement tool, for cleaning and/or debriding any parts of a dental implant, selected from the group consisting of dental fixture such as a screw, abutment, and dental restoration such as a crown, bridge or denture. Consequently, the present invention is also directed to the use of a composition of the invention for the preparation of a medicament and/or pharmaceutical and/or cosmetic composition for cleaning and/or debriding any parts of a dental implant, selected from the group consisting of dental fixture such as a screw, abutment, and dental restoration such as a crown, bridge or denture. Also, the invention is directed to a composition of the invention for use for cleaning and/or debriding any parts of a dental implant, selected from the group consisting of dental fixture such as a screw, abutment, and dental restoration such as a crown, bridge or denture.

The present invention further relates to the use of an antimicrobial and/or anti inflammatory composition according to the present invention, alternatively together with an implant cleaning and/or debridement tool, for cleaning and/or debriding orthopaedic implants, such as orthopaedic implants which are utilized for the preservation and restoration of the function in the musculoskeletal system, particularly joints and bones, including alleviation of pain in these structures, and/or for cleaning and/or debriding vascular stents, i.e. tubular implants arranged for insertion into blood vessels in order to prevent or counteract a localized flow constriction. Consequently, the present invention is also directed to the use of a composition of the invention for the preparation of a medicament for cleaning and/or debriding orthopaedic implants, such as orthopaedic implants which are utilized for the preservation and restoration of the function in the musculoskeletal system, particularly joints and bones, including alleviation of pain in these structures, and/or for cleaning and/or debriding vascular stents. Also, the invention is directed to a composition of the invention for use for cleaning and/or debriding orthopaedic implants, such as orthopaedic implants which are utilized for the preservation and restoration of the function in the musculoskeletal system, particularly joints and bones, including alleviation of pain in these structures, and/or for cleaning and/or debriding vascular stents.

The surface of medical implants such as e.g. dental implants, orthopaedic implants and vascular stents, or the vicinity thereof, has sometimes to be cleaned after placing. This is particularly important when an infection or contamination occurs, causing a progressive degenerative process in the bone adjacent to the implant known as periimplantitis. In these cases, the surface of the ailing implant has to be cleaned from microbes and contaminants to stop the progression of the disease and ensure re-integration of the implant. Failure to clean the implant surface will eventually lead to loss of bone and implant and make further alternative treatments difficult and sometimes even impossible. Furthermore, the surface of vascular stents may have to be cleaned during implantation in order to remove coagulum, and the interior of vascular stents, i.e. the cavity within vascular stents, may have to be cleaned in an endoscopic procedure during a later treatment due to restenosis, i.e. blocking of the blood vessel.

The present invention therefore relates to the use of an antimicrobial and/or anti-inflammatory composition according to the present invention, alternatively together with an implant cleaning and/or debridement tool, for cleaning and/or debriding an implant or the vicinity thereof after placing. Consequently, the present invention is also directed to the use of a composition of the invention for the preparation of a medicament for cleaning and/or debriding an implant or the vicinity thereof after placing. Also, the invention is directed to a composition of the invention for use for cleaning and/or debriding an implant or the vicinity thereof after placing.

In addition, for different reasons, it may be advantageous or necessary to debride surgically exposed hard tissue surfaces. For example, debriding of surgically exposed hard tissue surfaces may be advantageous or necessary to perform before regenerative treatment, i.e. in order to prepare the hard tissue surfaces for regenerative treatment. Examples of conditions, which may be associated with a treatment in which debridement of a surgically exposed hard tissue surface is advantageous or necessary to perform in order to prepare the surface for regenerative treatment, are: periimplantitis, periodontitis lesions, marginal periodontitis, apical periodontitis, furcation defects, apical granulomas and cysts, bone cysts, bone tumors, bone granulomas, bone cancers, (infected) extraction sockets, alveolitis sicca ("dry socket"), cleaning of apicectomy defects, localized osteomyelitis, trauma induced defects, resection or revision of implants, resection or revision of fractures, and removal of temporary bone implants (such as orthopaedic bone plates, retainers and screws). Furthermore, debridement of articular surfaces in joints affected by arthritis and debridement of such surfaces before regenerative treatment for cartilage and ligaments is instituted may also be advantageous or necessary to perform.

The present invention thus relates to the use of an antimicrobial and/or anti-inflammatory composition according to the present invention, alternatively together with an implant cleaning and/or debridement tool, for cleaning and/or debriding surgically exposed hard tissue surfaces before regenerative treatment. Consequently, the present invention is also directed to the use of a composition of the invention for the preparation of a medicament and/or a pharmaceutical and/or cosmetic composition for cleaning and/or debriding surgically exposed hard tissue surfaces before regenerative treatment. Also, the invention is directed to a composition of the invention for use for cleaning and/or debriding surgically exposed hard tissue surfaces before regenerative treatment.

The antimicrobial and/or anti-inflammatory composition according to the present invention, alternatively together with an implant cleaning and/or debridement tool, may be utilized during surgery for cleaning of the surface of a metallic medical implant after infection and/or bone resorption. For example, it may be utilized for cleaning the surface of a metallic dental implant and/or a metallic orthopaedic implant. Thus, it may be utilized for removing e.g. bacterial biofilm, debris, calculus or fibrous tissue from the surface of a dental implant, such as a titanium screw. Alternatively, it may be utilized together with a further cleaning agent (i.e. an antibacterial agent) in order to remove the bacterial biofilm from the vicinity of the dental fixture during implantation. It may also be utilized for cleaning the surface of, or the vicinity of, an abutment. Consequently, the present invention is also directed to the use of a composition of the invention for the preparation of a medicament for cleaning, e.g. removing bacterial biofilm, debris, calculus or fibrous tissue from the surface of a metallic dental implant, such as a titanium screw or an abutment, or a metallic orthopaedic implant. Also, the invention is directed to a composition of the invention for use for cleaning, e.g. removing bacterial biofilm, debris, calculus or fibrous tissue the surface of a metallic dental implant, such as a titanium screw or an abutment, or a metallic orthopaedic implant.

In addition, the antimicrobial and/or anti-inflammatory composition according to the present invention, alternatively together with an implant cleaning and/or debridement tool, may be utilized for removing cement remnants, bacterial biofilm, debris, calculus or fibrous tissue from the surface of an orthopaedic implant or for removing plaque from the surface of a vascular stent. Alternatively, it may be utilized for cleaning the interior of a vascular stent, i.e. the cavity within a vascular stent, in an endoscopic procedure during a later treatment due to restenosis, i.e. blocking of the blood vessel.

A procedure involving use of the antimicrobial and/or anti-inflammatory composition according to the present invention, alternatively together with an implant cleaning and/or debridement tool, may, for example, involve the steps of: surgically exposing a hard tissue surface to be treated; removal of inflamed soft tissue; debriding the surface by means of applying the antimicrobial and/or anti-inflammatory composition according to the present invention, alternatively together with an implant cleaning and/or debridement tool; applying (regenerative) treatment as needed; replacing soft tissue; suturing for good primary closure and wound stability; and allowing the wound to heal.

In particular, the antimicrobial and/or anti-inflammatory composition according to the present invention, alternatively together with an implant cleaning and/or debridement tool, is an efficient tool for debridement of surgically exposed tooth root surfaces, furcation defects and bony defects before regenerative treatment (i.e. by means of, for example Straumann® Emdogain, bone graft materials, autologous bone, membranes, etc.), the antimicrobial and/or anti-inflammatory composition according to the present invention, alternatively together with an implant cleaning and/or debridement tool, is especially effective for removing granulation tissue, and for removing concrements of calcified biofilms (plaques) and subgingival calcus.

The antimicrobial and/or anti-inflammatory composition according to the present invention, alternatively together with an implant cleaning and/or debridement tool, is advantageous to utilize for cleaning and/or debriding both "hard" metallic medical and/or dental implants having relatively hard surfaces, such as e.g. medical implants of steel, and "soft" metallic medical implants having delicate surfaces, such as e.g. medical and/or dental implants of titanium, a titanium alloy, zirconium or a zirconium alloy.

In addition, the antimicrobial and/or anti-inflammatory composition according to the present invention does not leave contaminants, i.e. material residues, incompatible with reintegration of the implanted structure. Thus, the inflammation risk is minimal.

In particular, a relatively rapid debridement procedure of surfaces, which are otherwise hard to clean and/or hard to reach by hand instrumentation, may be performed by means of the antimicrobial and/or anti-inflammatory composition according to the present invention, alternatively together with an implant cleaning and/or debridement tool. Rapid treatment ensures a better treatment outcome. As mentioned above, it is a well-known fact that the morbidity and frequency of adverse effects, such as e.g. post-surgery effects, are directly related to, and often proportional to, the time used for the debridement of surgically exposed hard tissue surfaces. Thus, rapid debridement treatment ensures a better total treatment outcome.

The use of the antimicrobial and/or anti-inflammatory composition according to the present invention, alternatively together with an implant cleaning and/or debridement tool, is especially favorable where the treatment plan for a defect includes placing of a titanium implant or any other device made of titanium, since only titanium and no other metallic ions or polymers that can provoke unwanted and/or adverse clinical and/or biological effects can contaminate the treated area, hampering the outcome of planned and/or future implant procedures.

Oral Hygiene

In oral hygiene and dentistry, debridement refers to the removal of plaque and calculus that have accumulated on the teeth, which can be performed routinely by the technician, for medical, hygienic, as well as for purely cosmetic reasons. Thus, in one embodiment, the antimicrobial and/or anti-inflammatory composition according to the present invention, again alternatively together with an implant cleaning and/or debridement tool, is used for removal of plaque and calculus that have accumulated on the patient's natural teeth, or tooth implants. The antimicrobial and/or anti-inflammatory composition according to the present invention comprises radicalized oxygens and is thus particularly suitable for use in the bleaching of natural and/or artificial teeth.

Microorganisms

An antimicrobial and/or anti-inflammatory composition according to the present invention is in general intended for use in debriding and/or cleaning a biological surface and/or a biomaterial surface in situ, e.g. for use in removal of biofouling, biofilm and/or necrotic tissue from such a biological surface and/or a biomaterial surface in situ.

Biofilms that can be prevented, eliminated and/or treated by the composition of the present disclosure include, but are not limited to, biofilms present within the oral cavity, e.g., on the surface of teeth, on the surface of mucosal/soft-tissues such as gingivae/periodontium and inside a tooth canal (e.g. the endodontic canal).

In certain embodiments, biofilms that can be prevented, eliminated and/or treated by the composition of the present disclosure include biofilms on the urinary tract, lung, gastrointestinal tract, on and/or within chronic wounds, and present on the surface (e.g., implants) and within medical devices and medical lines, e.g., catheters, medical instruments and medical tubing.

The composition of the present disclosure can be used to reduce the growth and/or inhibit the viability of one or more microorganisms, e.g., bacteria in a biofilm. For example, and not by way of limitation, the bacteria can include *Streptococcus* mutctns (S. mutctns), *Streptococcus sobrinus, Streptococcus* sctnguis (sctnguinis), *Streptococcus gordonii, Streptococcus omlis, Streptococcus mitis, Actinomyces odontolyticus, Actinomyces viscosus,* Aggregcttibctcter ctctinomycetemcomitctns, Ictctobctcillus spp., Porphyromoncts gingivctlis, Prevotellct *intermedia, Bacteroides forsythus, Treponema denticola, Fusobacterium nucleatum, Campylobacter rectus, Eikenella corrodens, Veillonella* spp., *Micromonas micros, Porphyromonas* cangingivalis, *Haemophilus actinomycetemcomitans Actinomyces* spp., *Bacillus* spp., *Mycobacterium* spp., *Fusobacterium* spp., *Streptococcus* spp., *Staphylococcus aureus, Streptococcus pyogenes, Streptococcus agalectiae, Proteus mirabilis, Elebsiella pneumoniae, Acinetobacter* spp., *Enterococcus* spp., *Prevotella* spp., *Porphyromonas* spp., *Clostridium* spp., *Stenotrophomonas maltophilia,* P. cangingivalis, *Candida albicans, Escherichia coli* and/or *Pseudomonas aeruginosa.* In certain embodiments, the bacteria are *S. mutans,* which is present within biofilms found in the oral cavity, e.g., on the surface of teeth.

The microorganisms most commonly associated with implant failure are spirochetes and mobile forms of Gram-negative anaerobes. Diagnosis can be based on changes of colour in the gum, bleeding and probing depth of peri-implant pockets, suppuration, x-ray and gradual loss of bone height around the tooth. The antibiotic therapy proven to be most efficacious in the antibiogram has so far been the association of amoxycillin and clavulanic acid. In addition to bacterial infections, microbial infections in the oral cavity can of course also include fungal and/or viral infections.

An antimicrobial and/or anti-inflammatory composition according to the present invention is effective for killing bacteria, fungus and/or virus.

What is more, the composition described herein is anti-microbial, without causing microbial resistance, as well as anti-inflammatory.

In consequence, the present invention relates to a method for treating and/or preventing periimplantitis, gingivitis and/or mucositis, peri-implant mucositis and/or periodontitis, comprising cleaning and/or debriding a biological surface and/or a biomaterial surface in situ by applying a composition according to the present invention to said fouled, filmed and/or necrotized surface.

EXAMPLES

The following Examples have been included to provide guidance to one of ordinary skill in the art for practicing representative embodiments of the presently disclosed subject matter. Considering the present invention and the general level of skill in the art, those of skill can appreciate that the following Examples are intended to be exemplary only and that numerous changes, modifications, and alterations can be employed without departing from the scope of the presently disclosed subject matter.

Example 1

Methylene Blue Degradation when Mixed with $H_2O_2$ at 3% v/vv/v and Fluoride Releasing at Various Concentrations Methylene blue (MB) is a heterocyclic aromatic chemical compound with molecular formula: $C_{16}H_{18}N_3SCl$ (SigmaAldrich, Oslo, Norway). It has many uses in a range of different fields, such as biology and chemistry. MB exemplifies organic materials and can thus be used as agent to simulate bacteria as seen in several publications and is commonly used when investigating the degradative properties of $H_2O_2$. A degradation of MB therefore can be used as a model for the in vivo degradation of organic material, such as bacteria, or dead, damaged, and/or infected tissue. At room temperature, it appears as a solid, odourless, dark green powder, that yields a blue solution when dissolved in water. When degraded in solution, methylene blue becomes colourless.

When methylene blue is analysed by UV-vis spectrophotometry (Lambda 25, Perkin Elmer, USA), it absorbs light at 690 cm. This machine was used to quantify the degradation of MB.

The aim was to measure if methylene blue could be degraded by $H_2O_2$(PERDROGEN® 30% $H_2O_2$ (v/v), Sigma Aldrich AS, Oslo, Norway) at 5% only, without ACP in a composite hydrogel formulation comprising poloxamers (Sigma Aldrich AS, Oslo, Norway) at a concentration of 5% w/v. Then, an increasing concentration of amorphous calcium phosphates ACP (by mixing two precursor components. Component A contained MB in a mixture of mono- and dibasic ammonium phosphate at pH 5.5.) was added to the solution until a maximum concentration of 8 g/L.

The measurements were taken every 3 minutes for one hour. The pH of the suspension containing MB was also registered. The suspension was stirred prior to each measurement to prevent the deposition of the ACP particles.

Almost no degradation was found when only $H_2O_2$(PERDROGEN® 30% $H_2O_2$ (v/v), Sigma Aldrich AS, Oslo, Norway) at 15% v/vv/v was mixed with MB. Surprisingly, the presence of ACP at 0.25 g/L in the suspension made the MB degradation possible. Increasing the concentration of ACP particles in the suspension increased the MB degradation. Increasing the concentration of ACP particles decreased slightly the pH from 3.7 without ACP, to 2.8 with ACP at 1 M.

The $H_2O_2$ alone could not break down the MB molecules; surprisingly ACP must be present to reach this purpose.

Example 2

Methylene Blue Degradation when Mixed with $H_2O_2$ at 7% and ACP at Various Concentrations The aim was to measure if methylene blue could be degraded by ACP nanoparticles only (synthesized by chemical from Sigma Aldritch, mixture of mono- and dibasic ammonium phosphate at pH 5.5), without $H_2O_2$ in composite hydrogel formulation comprising poloxamers (Sigma Aldrich AS, Oslo, Norway) at a concentration of 5% w/v. Then, an increasing concentration of $H_2O_2$(PERDROGEN® 30% $H_2O_2$ (v/v), Sigma Aldrich AS, Oslo, Norway) was added to the suspension until a maximum concentration of 7% v/v. The procedure of the experiment was the same as explained in example 1.

The results are not shown. Almost no degradation was found when only ACP at 0.5 g/L was mixed with MB. Adding 5% v/vv/v concentrated $H_2O_2$ increased the MB degradation. Increasing the concentration of $H_2O_2$ in the suspension increased the MB degradation in a linear way. Increasing the concentration of $H_2O_2$ decreased the pH from 4.9 without $H_2O_2$, to 3.3 with $H_2O_2$ at 15% v/v.

The ACP alone could not break down the MB molecules; $H_2O_2$ must be present to reach this purpose.

Example 3

Methylene Blue Degradation when Mixed with the Suspension of $H_2O_2$ at 5% in Composite Hydrogel Formulation Comprising Poloxamers (Sigma Aldrich AS, Oslo, Norway) at a Concentration of 5% w/v. With Synthetic Octa Calcium Phosphate (OCP) and with Fluoride Substitute Calcium Phosphate (F-CaP)

From examples 1 and 2, $H_2O_2$(PERDROGEN® 30% $H_2O_2$ (v/v), Sigma Aldrich AS, Oslo, Norway) and synthetic octacalcium phosphate (OCP) and with fluoride substitute OCP concentrations in composite hydrogel formulation comprising poloxamers (Sigma Aldrich AS, Oslo, Norway) at a concentration of 5% w/v. were chosen in order to create a suspension that uses this synergic effect but as well which could be used in a physiological environment ($[H_2O_2]<6\%$ v/v and pH>3). Synthetic OCP and two types of fluoride-containing apatitic calcium phosphates (referred to as F-CaP hereafter) were prepared following the methods previously reported. Briefly, fluoride-containing apatitic calcium phosphates by hydrolysis with F- (referred to as HF-CaP hereafter) were synthesized by incubating OCP powders in a 150 mM Tris buffer containing 50 ppm F- (as sodium fluoride: NaF) at 37° C. The initial pH of the buffer was varied from 7.1 to 9.9. The incubation of HF-CaP continued for 10 or 60 min. In contrast, fluoride-containing apatitic calcium phosphates from co-precipitation with F- (referred to as CF-CaP hereafter) were prepared by applying the co-precipitation of OCP in the presence of F-. A calcium acetate solution was added to sodium hydrogen phosphate solution according to a synthesis method previously described, which contained F- (as NaF) for 30 min at 70° C. The F- concentration that was initially used was in the 12-230 ppm range. All recovered samples were washed several times with distilled water and dried at 105° C. overnight The aim was to discover whether or not NaCl and NaF salts could further increase the MB degradation when introduced in the chosen suspension. The results are not shown.

Interestingly, doping the suspension with NaCl reduced the MB degradation by half compared with the suspension with only OCP and $H_2O_2$. Substituting with F (Sigma Aldrich AS, Oslo, Norway) was even stronger in reducing the MB degradation, almost preventing this degradation to occur compared with the suspension with only OCP and $H_2O_2$.

Doping the $H_2O_2$/OCP suspension with NaF (Sigma Aldrich AS, Oslo, Norway) and NaCl (Sigma Aldrich AS, Oslo, Norway) salts did not increase the MB degradation.

Changes in Ca2+ and inorganic phosphate ion concentrations on the F-CaP coatings The concentration of Ca2+ and inorganic phosphate ion (Pi) in the culture medium was determined using Calcium E and Phosphor C tests (Wako Pure Chemical Industries, Osaka, Japan), respectively. One hundred microliters of α-MEM containing 10% FBS was added to each well of a 96-well tissue culture plate with F-CaP or OCP coating. After the plates had been incubated for 3 days at 37° C. in a 5% carbon dioxide environment, the supernatants were collected for Ca2+ and Pi quantitative analyses.

The dissolution behaviours of F-CaP or OCP particles were performed after 3 days of incubation with α-MEM at 37° C. The Ca2+ concentrations of the HF1.80-CaP and HF3.33-CaP supernatants were dramatically reduced relative to the no coating control. Conversely, the Ca2+ concentration of medium from the CF-CaP coating was equal to or slightly greater than that of OCP.

Example 4 pH Measurements of Various Suspensions of Composite Hydrogel Formulation Comprising Poloxamers (Sigma Aldrich AS, Oslo, Norway) at a Concentration of 10% w/v.

The pH in wound healing is an important factor, and the suspension's pH can be altered by different calcium phosphate (from examples 3) concentrations and other added components.

A laboratory pH meter (pH Meter Lab 850 Set with Blueline 14 pH Electrode, Scott Glass Ltd, Stafford, UK) was used to measure the pH in different solutions. Below is a list of the resulting pH after the given concentrations:

1. A mixture of 5% v/v$H_2O_2$ and 1.6 g/L1.6 g/L ACP resulted in a pH=4.4±0.1.
2. A mixture of 5% v/v$H_2O_2$+1.6 g/L HA resulted in a pH=5.2±0.1
3. A mixture of 5% v/v$H_2O_2$ 2+1.6 g/L CaPF resulted in a pH=6.1±0.0
4. A mixture of 5% v/v$H_2O_2$+1.6 g/L OCP-F+1.6 g/L ACPresulted in a pH=A 4.2±0.1
5. A mixture of 5% $H_2O_2$+1.6 g/L HA-F+1.6 g/L ACP resulted in a pH=5.9±0.0

The range of the various tested suspension went from 4.2 up to 6.1.

Example 5

Suspension with Different Calcium Phosphates

The solution of 2 g/L of different calcium phosphates were purchased from Sigma Aldrich (Hydroxylapatite, Calcium hydroxyphosphate, Hap $Ca_{10}(PO_4)_6(OH)_2$, Tribasic calcium phosphate $[Ca_5(OH)(PO_4)_3]_x$, p-TCP, p-Tricalcium phosphate $Ca_3O_8P_2$, α-Tricalcium phosphate $Ca_3O_8P_2$ and compared with the CaPs from examples 1-4 and mixed with 3 vol. % $H_2O_2$(PERDROGEN® 30% $H_2O_2$ (v/v), Sigma Aldrich AS, Oslo, Norway) from example 1 and 2.

The amounts of calcium in different compositions were determined using atomic absorption spectroscopy (AAS; AANALYST 400, Perkin Elmer, USA). AAS samples were acidified with HCl to dissolve precipitated mineral before lanthanum chloride was added at a concentration of 10 mg/mL to precipitate phosphate. Acetylene was used as carrier gas. Three independent samples were measured per data point.

Example 6

Anti-Bacterial Effect of Ca-P Particles ON *Staphylococcus aureus*

This example describes the anti-bacterial potential of the activated CA-P particles.

Bacteria:

*Staphylococcus aureus* (*S. aureus*) are important human commensal and opportunistic pathogens responsible for a wide range of infections. They are one of the most known bacteria responsible for post-surgery infection. Therefore, *S. aureus* was chosen for this experiment.

Procedure:

The anti-bacterial effect of the three gels was treated with a suspension of $H_2O_2$ (PERDROGEN® 30% $H_2O_2$ (v/v), Sigma Aldritch AS, Oslo, Norway) at 1, 2 and 5% v/v that was mixed with CaPs for, example 5 at 0.5, 1.6 and 20 g/L. The control was poloxamer gel without any particles.

These gels will prior to the mixing of suspension loaded with 500 μl from a broth of *S. aureus* was diluted in 4 ml of PBS (Dulbecco's PBS, Sigma-Aldrich, St Louis, MO, USA) (stock solution). A drop of 10 μl of this stock solution was placed on the top of the gels. Once the UV light exposure of the test groups reached, the small squares of gels was individually placed in 1.5 ml Eppendorf tubes containing 500 μl of cell culture medium (without antibiotics) of from Invitrogen (GIBSCO MEM, Invitrogen, Carlsbad, CA, USA). All the Eppendorf tubes containing the gels and the bacteria was placed in an incubator, in the dark, at 37° C. for 20 hours. After 20 hours, all the samples were taken out of the incubator. A Spectrometer (Perkin Elmer UV-Vis 200, Oslo, Norway) was calibrated with only 700 μl of cell media for the base line. Then, the three Eppendorf tubes containing only 500 μl of cell media+10 μl of the stock solution was analysed. Then, one by one the test tubes were shaken and a volume of 400 μl from each tube was mixed with 300 μl of cell media. The 1.5 ml cuvettes contained 700 μl of liquid to be analysed.

The results showed that the presents of CaP particles did not alter the change the anti-bacterial properties Example 7

Anti-Bacterial Effect of Ca-p Particles on *Pseudomonas aeroginosa* Bacteria

This example describes the anti-bacterial potential of the Ca-P particles as described in examples 4.

Bacteria:

*Pseudomonas aeroginosa* bacteria are opportunistic pathogens responsible for a wide range of infections, and often found in chronical wounds.

Procedure:

The anti-bacterial effect of the different gels was treated with a suspension of 3%, 5% and 7% $H_2O_2$(PERDROGEN® 30% $H_2O_2$ (v/v), Sigma Aldritch AS, Oslo, Norway) in poloxamer gels with concentration (0.1, 1 and 5% v/v) that was be mixed with Ca-Ps (examples 4) at 0.5, 2 and 5 g/L. The control was gels without any suspension. These gels will prior to the mixing of suspension loaded with 500 μl from a broth of *S. aureus* was diluted in 4 ml of PBS (Dulbecco's PBS, Sigma-Aldrich, St Louis, MO, USA) (stock solution). A drop of 10 μl of this stock solution was placed on the top of the gels. Once the UV light exposure of the test groups reached, the small squares of gels was individually placed in 1.5 ml Eppendorf tubes containing 500 μl of cell culture medium (without antibiotics) of from Invitrogen (GIBSCO MEM, Invitrogen, Carlsbad, CA, USA). All the Eppendorf tubes containing the gels and the bacteria was placed in an incubator, in the dark, at 37° C. for 20 hours. After 20 hours, all the samples was taken out of the incubator. A Spectrometer (Perkin Elmer UV-Vis 200, Oslo, Norway) was calibrated with only 700 μl of cell media for the base line. Then, the three Eppendorf tubes containing only 500 μl of cell media+10 μl of the stock solution was analysed. Then, one by one the test tubes were shaken and a volume of 400 μl from each tube was mixed with 300 μl of cell media. The 1.5 ml cuvettes contained 700 μl of liquid to be analysed.

Example 8

Anti-Bacterial Effect of Bioceramics Particles on *Escherichia coli* Bacteria

This example describes the anti-bacterial potential of the various bioceramics

Bacteria:

*E. coli* bacteria are sometime present in chronical wounds.

Procedure:

The anti-bacterial effect of the three gels was tested with a suspension of $H_2O_2$ (PERDROGEN® 30% $H_2O_2$ (v/v), Sigma Aldritch AS, Oslo, Norway) at 3.5 and 7.5 that was mixed with $ZrO_2$ and $TiO_2$ (Aeroxide P25, Evonik AG, Essen, Germany) at 0.5, 1.6 and 20 g/L. The control was gels without any suspension and gels with treated only $H_2O_2$ (PERDROGEN® 30% $H_2O_2$ (v/v), Sigma Aldritch AS, Oslo, Norway) at 5% v/v) in poloxamer gels with concentration (0.1, 1 and 5% v/v).

These gels will prior to the mixing of suspension loaded with 500 μl from a broth of *S. aureus* was diluted in 4 ml of PBS (Dulbecco's PBS, Sigma-Aldrich, St Louis, MO, USA) (stock solution). A drop of 10 μl of this stock solution was placed on the top of the gels. Once the UV light exposure of the test groups reached, the small squares of gels was individually placed in 1.5 ml Eppendorf tubes containing 500 μl of cell culture medium (without antibiotics) of from Invitrogen (GIBSCO MEM, Invitrogen, Carlsbad, CA, USA). All the Eppendorf tubes containing the gels and the bacteria was placed in an incubator, in the dark, at 37° C. for 20 hours. After 20 hours, all the samples was taken out of the incubator. A Spectrometer (Perkin Elmer UV-Vis 200, Oslo, Norway) was calibrated with only 700 μl of cell media for the base line. Then, the three Eppendorf tubes containing only 500 μl of cell media+10 μl of the stock solution was analysed. Then, one by one the test tubes were shaken and a volume of 400 μl from each tube was mixed with 300 μl of cell media. The 1.5 ml cuvettes contained 700 μl of liquid to be analysed.

The presences of $ZrO_2$ did not alter the antibacterial activities, whereas surprisingly, the presences of $TiO_2$ did. The effect was linear upon concentrations.

Example 9

Anti-Bacterial Effect of Activated Bioglas Doped with Fluorine ON *Staphylococcus aureus*

This example describes the anti-bacterial potential of the Bioglass™ 45S5 (MOSCI Corp. Rolla Missouri MO 65401) and mixed in suspension of $H_2O_2$ (PERDROGEN® 30% $H_2O_2$ (v/v), Sigma Aldritch AS, Oslo, Norway) at 3.5 and 7.5 that was mixed with the Bioglass™ 45S5 at 0.5, 1.6 and 20 g/L.

Bacteria:

*Staphylococcus aureus* (*S. aureus*) are important human commensal and opportunistic pathogens responsible for a wide range of infections. They are one of the most known bacteria responsible for post-surgery infection. Therefore, *S. aureus* was chosen for this experiment.

Procedure:

The anti-bacterial effect of the gels was treated with a suspension of $H_2O_2$ (PERDROGEN® 30% $H_2O_2$ (v/v), Sigma Aldrich AS, Oslo, Norway) at 5% v/v that was mixed with bioglass at various concentrations. In addition, this suspension was doped with fluorine with 0.01, 0.5, 1 and 3 atomic weight % fluorine. The doping was done by added the equivalent amount of NaF into the suspension. The amount of fluorine on the surface was detected and quantified with X-ray Photospectrometry (XPS). The control was gels without any suspension and gels with treated only $H_2O_2$(PERDROGEN® 30% $H_2O_2$ (v/v), Sigma Aldritch AS, Oslo, Norway) at 5% v/v.

These gels will prior to the mixing of suspension loaded with 500 µl from a broth of *S. aureus* was diluted in 4 ml of PBS (Dulbecco's PBS, Sigma-Aldrich, St Louis, MO, USA) (stock solution). A drop of 10 µl of this stock solution was placed on the top of the gels. Once the UV light exposure of the test groups reached, the small squares of gels was individually placed in 1.5 ml Eppendorf tubes containing 500 µl of cell culture medium (without antibiotics) of from Invitrogen (GIBSCO MEM, Invitrogen, Carlsbad, CA, USA). All the Eppendorf tubes containing the gels and the bacteria was placed in an incubator, in the dark, at 37° C. for 20 hours. After 20 hours, all the samples were taken out of the incubator. A Spectrometer (Perkin Elmer UV-Vis 200, Oslo, Norway) was calibrated with only 700 µl of cell media for the base line. Then, the three Eppendorf tubes containing only 500 µl of cell media+10 µl of the stock solution was analysed. Then, one by one the test tubes were shaken and a volume of 400 µl from each tube was mixed with 300 µl of cell media. The 1.5 ml cuvettes contained 700 µl of liquid to be analysed. The results show that the number of particles had little effect on the antibacterial properties, whereas the most dominating factor was amount of poloxamer gel and $H_2O_2$.

Example 10

Removal of Biofilm

This example describes the anti-bacterial potential of the poloxamer gels with concentration (0.1, 1 and 5% v/v). In vitro testing: biomass assessment after cleaning Samples Preparation Chemically pure (cp) titanium disks with a diameter of 6.2 mm and a height of 2 mm were used. They had a similar machined surface topography (turned with ripple). After production, the disks were washed with NaOH at 40% v/v and $HNO_3$ at 50% v/vin an ultrasonic bath to remove contaminants, then were washed with deionised water to reach a neutral pH and stored at room temperature in 70% v/v ethanol. Thereafter, the coins were placed in Eppendorf tube and steam autoclaved for sterilization.

Four chemical decontamination agents were selected for the in vitro testing: sterile saline $H_2O$ (VWR, Oslo, Norway), Chlorhexidine, 3% v/v $H_2O_2$(VWR, Oslo, Norway), a mixture of 3% v/v $H_2O_2$ and 2 g/L $TiO_2$ (2 g nano-particles: P25 Aeroxide, Degussa Evonik, Evonik Industries AG, Essen, Germany).

Inoculation, Cleaning and Analysis 15 sterile titanium disks per groups were inoculated. The control group was inoculated with brain heart infusion broth (BHI) only, while the test groups (four) were inoculated with the bacteria culture (10 µl *Staphylococcus epidermidis*+5 ml BHI). The incubation time was set at 24 h at 35° C. in an aerobic atmosphere. The discs were then be transferred to new wells, rinsed with sterile saline water, then exposed to the four selected chemical agents for two minutes, then rinsed again with sterile saline water. The amount of biofilm present on the surface of the titanium samples was assessed by using the safranin staining method: 10 min exposure to a 0.1% solution of safranin, then rinsed with distilled water, air dried, and exposed to a solution of 30% acetic acid to release the colored biomass from the titanium surfaces. The intensity of the staining was analyzed using a Synergy HT Multi-Detection Microplate Reader (Biotek, VT, USA) with a wavelength of 530 nm.

Results

Optical density analysis in the Synergy HT Multi Detection microplate Reader revealed that the samples exposed the mixture of 3% v/v $H_2O_2$ and different gel concentrations were significantly different than the control. Moreover, higher poloxamer concentration and higher hydrogen peroxide concentration increased the biofilm removal.

Example 11

Re-Growth of Biofilm after Exposure to Activated $Tio_2$ Microparticles

This example describes the anti-bacterial potential of the activated $TiO_2$ microparticles in preventing biofilm re-growth after disinfection.

In Vitro Testing: Bacteria Re-Growth

Another test was conducted in order to determine the viability of the biofilm after the disinfection. The method was similar than for the safranin staining analysis conducted in example 10 above, from the inoculation to the disinfection using the same four products. But this time, after the disinfection step, the samples was rinsed in NaCl and re-incubated at 35° C. for four hours in pure BHI medium. The medium was collected and analyzed using the same spectrophotometer than for the safranin staining but this time at a wavelength of 600 nm. The intensity of the absorbance was compared between control and test groups.

The results from this experiment should show a significantly lower level of bacteria re-growth on the samples exposed to the mixture of 3% v/v $H_2O_2$ and 2 g/L $TiO_2$ compared to the control group and to the samples exposed to $H_2O_2$ alone.

Example 12

Application for Periodontitis Treatment

The two-component poloxamer-Peroxide gel described here is intended for debridement of teeth by topical application. Debridement is the medical removal of dead, damaged, or infected tissue to improve the healing potential of the remaining healthy tissue. In oral surgery and dentistry, debridement also refers to the removal of biofilm/plaque accumulated on the tooth roots (taking into account that plaque can also be considered a mineralized biofilm). The gel helps the debridement of teeth; it effectively increases the effectiveness of mechanical removal of biofilm/plaque from tooth surface; biofilm/plaque causing inflammatory situations, and the removal therefore brings advantages with regard to the following aspects:

Attenuation of degradation of dental tissues

Attenuation of inflammation

Attenuation of the onset of periodontitis, bone damage and loss of teeth

The intended use of the device is systematic professional use in treatment of periodontitis and for patients at risk for the above listed problems.

The gel device can be used as part of any debridement procedure, used alone or as an adjuvant to a mechanical removal remedies (a specific toothbrush, hand instrument or motorized device for example). There are no incompatibilities of the product with the materials that make up the most common brushes, or with materials used in reconstructive or aesthetic dentistry.

Mixing the gel:

1) The contents of the syringe must be completely injected into the vial containing the hydrogen peroxide:
2) Shake the vial to aid mixing, without removing the syringe;
3) Draw the mixture into the syringe, remove the vial and screw the tip tightly in the Luer-lock connection and use it directly to apply the gel in the areas of interest;

The mixed gel must be used within 20 minutes. This is because the active hydrogen peroxide loses its efficacy after this. The loss of activity does not pose any hazard to patient or environment as the peroxide and gel decomposes to water carbon dioxide and oxygen.

Use of Poloxamer-Peroxide Gel in Periodontal Surgery:

1. Following reflection of mucoperiosteal flaps in the area selected for periodontal surgery, the exposed root surfaces are mechanically debrided in order to remove any excess plaque and/or calculus.
2. The gel is then topically applied onto the ex-posed and debrided root/implant surfaces for 2 minutes. Apply the gel onto those parts of the surfaces which will be covered by soft tissues once flaps are replaced and sutured.
3. Active rubbing (<burnishing) may be applied by a hand instrument, a brush like a brush, an ultrasound device or any other motorized device of choice, laser or compressed air as these reduces the efficacy of the gel.
4. After debridement, the root surfaces and the adjacent tissues must be rinsed thoroughly with sterile saline solution.
5. Apply regenerative therapy device(s) if planned.
6. Reposition flap and stabilize with sutures. There are no extraordinary post-operative precautions when the gel is used.
7. Care should be taken to avoid recontamination of the conditioned root/implant surfaces after the final rinse and prior to treatment with regenerative products.

Example 13

Application for Peri-Implantitis Treatment

The two-component poloxamer-Peroxide gel described here is intended for debridement of implanted implants by topical application. Debridement is the medical removal of dead, damaged, or infected tissue to improve the healing potential of the remaining healthy tissue. In oral surgery and dentistry, debridement also refers to the removal of biofilm/plaque accumulated on the implant surface (taking into account that plaque can also be considered a mineralized biofilm). The gel helps the debridement of implants; it effectively increases the effectiveness of mechanical removal of biofilm/plaque from implant surface; biofilm/plaque causing inflammatory situations, and the removal therefore brings advantages with regard to the following aspects:

Attenuation of degradation of peri-implant tissues

Attenuation of local inflammation

Attenuation of the onset of peri-implantitis, bone damage and loss of implants

The intended use of the device is systematic professional use in surgical treatment of periimplantitis in for patients at risk for the above listed problems.

The gel can be used as part of any debridement procedure, used alone or as an adjuvant to a mechanical removal remedies (a specific toothbrush, hand instrument or motorized device for example). There are no incompatibilities of the product with the materials that make up the most common brushes, or with materials used in reconstructive or aesthetic dentistry.

Mixing the Gel:

1) The contents of the syringe must be completely injected into the vial containing the hydrogen peroxide
2) Shake the vial to aid mixing, without removing the syringe
3) Draw the mixture into the syringe, remove the vial and screw the tip tightly in the Luer-lock connection and use it directly to apply the gel in the areas of interest The mixed gel must be used within 20 minutes. This is because the active hydrogen peroxide loses its efficacy after this. The loss of activity does not pose any hazard to patient or environment as the peroxide and gel decomposes to water carbon dioxide and oxygen.

Use of Poloxamer-Peroxide Gel in Peri-Implantitis Surgery:

1. Following reflection of mucoperiosteal flaps in the area selected for peri-implant surgery, the exposed implant surfaces are mechanically debrided in order to remove any excess plaque and/or calculus.
2. The mixed gel is then topically applied onto the exposed and debrided implant surfaces for 2 minutes. Apply the gel onto those parts of the surfaces which will be covered by soft tissues once flaps are replaced and sutured.
3. Active rubbing (<burnishing) may be applied by a hand instrument, a brush like TiBrush, an ultrasound device or any other motorized device of choice. Avoid using implantoplasty, laser or compressed air as these reduces the efficacy of the gel.
4. After debridement, the root/implant surfaces and the adjacent tissues must be rinsed thoroughly with sterile saline solution.
5. Apply regenerative therapy device(s) if planned.
6. Reposition flap and stabilize with sutures. There are no extraordinary post-operative precautions when the gel is used.
7. Care should be taken to avoid recontamination of the conditioned implant surfaces after the final rinse and prior to treatment with regenerative products.

Example 14

Application for Peri-Implant Mucositis and Gingivitis

The two-component poloxamer-Peroxide gel described here is intended for debridement of teeth and implanted implants by topical application. Debridement is the medical removal of dead, damaged, or infected tissue to improve the healing potential of the remaining healthy tissue. In oral surgery and dentistry, debridement also refers to the removal of biofilm/plaque accumulated on the tooth roots and implants (taking into account that plaque can also be considered a mineralized biofilm). The gel helps the debridement of teeth; it effectively increases the effectiveness of mechanical removal of biofilm/plaque from tooth/implant surface; biofilm/plaque causing inflammatory situations, and the removal therefore brings advantages with regard to the following aspects:

- Attenuation of degradation of periodontal and per-implant tissues
- Attenuation of local inflammation
- Attenuation of the onset and progression of periodontitis and peri-implantitis, causing loss of bone, teeth and implants The intended use of the device is systematic professional use in periodic oral hygiene for patients at risk for the above listed problems.

Nu Bone® Clean can be used as part of any debridement procedure, used alone or as an adjuvant to mechanical removal remedies (a specific toothbrush, hand instrument or motorized device for example). There are no incompatibilities of the product with the materials that make up the most common brushes, or with materials used in reconstructive or aesthetic dentistry.

Mixing the Gel:

1. The contents of the syringe must be completely injected into the vial containing the hydrogen peroxide.
2. Shake the vial to aid mixing, without removing the syringe.
3. Draw the mixture into the syringe, remove the vial and screw the tip tightly in the Luer-lock connection and use it directly to apply the gel in the areas of interest The mixed gel must be used within 20 minutes. This is because the active hydrogen peroxide loses its efficacy after this. The loss of activity does not pose any hazard to patient or environment as the peroxide and gel decomposes to water carbon dioxide and oxygen.

The recommended methods of use for non-invasive applications against peri-implant mucositis and gingivitis are:

1. After removal of supragingival plaque and tartar the gel is mixed and applied carefully into the periodontal pocket using a narrow tip. Be careful not to apply too much pressure to avoid soft tissue damage. There should be a slight ischemia of the gingiva at the application site due to application pressure, but not any pain or bleeding.
2. After application, let the gel sit for one minute, then use a debridement tool of choice, typically a hand instrument, an ultrasound device or a brush, to clean the exposed surface of the tooth/implant.
3. After mechanical cleaning is completed rinse off any remaining gel with water-spray and suction.
4. The patient can rinse with water as normal after the procedure. There are no extraordinary postoperative precautions.

Example 15

Application for Prophylaxis and Maintenance Treatment Against Peri-Implant and Periodontal Disease and Conservation of Peri-Implant and Periodontal Health The two-component poloxamer-Peroxide gel described here is intended for prophylactic cleaning of teeth by topical application to keep peri-implant tissues and gingiva healthy. The gel helps the cleaning of teeth and implants and increases the effectiveness of mechanical removal of biofilm/plaque from tooth/implant surface; biofilm/plaque causing inflammatory situations, and the removal therefore brings advantages with regard to the following aspects:

- Attenuation of inflammation in peri-implant and periodontal tissues
- Protection against the onset of periodontal and peri-implant disease The intended use of the device is systematic professional use in periodic oral hygiene for patients at risk for the above listed problems or as maintenance treatment after surgical interventions to avoid relapse.

The gel can be used as part of any cleaning procedure, used alone or as an adjuvant to a mechanical removal remedies (a specific toothbrush, hand instrument or motorized device for example). There are no incompatibilities of the product with the materials that make up the most common brushes, or with materials used in reconstructive or aesthetic dentistry.

Mixing the Gel:

1. The contents of the syringe must be completely injected into the vial containing the hydrogen peroxide.
2. Shake the vial to aid mixing, without removing the syringe.
3. Draw the mixture into the syringe, remove the vial and screw the tip tightly in the Luer-lock connection and use it directly to apply the gel in the areas of interest.

The mixed gel must be used within 20 minutes. This is because the active hydrogen peroxide loses its efficacy after this time. The loss of activity does not pose any hazard to patient or environment as the peroxide and gel decomposes to water carbon dioxide and oxygen.

The recommended method of use for non-invasive prophylaxis and maintenance treatment are like this:

1. After removal of supragingival plaque and tartar the gel is mixed and applied carefully around the crevicular sulcus and into any gingival pockets that surround the teeth/implants to be treated, using a narrow applicator tip. Be careful not to apply too much pressure to avoid soft tissue damage when applying the gel into deep pockets.
2. After application, let the gel sit for one to three minutes to work. Do not use any instruments during this time. The gel will chemically clean the area of interest.
3. After the cleaning time has ended, the gel should be removed with water spray and suction.
4. If necessary, repeat the procedure until surface is visually clean.
5. The patient can rinse with water as normal after the procedure. There are no extraordinary postoperative precautions.

Example 16

Application for Debridement of Chronic Dermal Ulcers

The two-component poloxamer-Peroxide gel described here is intended for debridement of chronic ulcers of the skin by topical application. Debridement is the medical removal of dead, damaged, or infected tissue to improve the healing potential of the remaining healthy tissue. In wound care, debridement also refers to the removal of microbial biofilms accumulated on the wound surface. The gel helps the debridement of a wound; it effectively increases the effectiveness of mechanical removal of biofilm from the wound surface and at the same time increases the local level of oxygen. The microbial biofilm can cause inflammatory situations, and the removal therefore brings advantages with regard to the following aspects:

Attenuation of degradation of epithelial and connective tissues

Attenuation of local inflammation

Attenuation of the onset of infection, necrosis and wound progression

The intended use of the device is systematic professional use in repeated treatment of chronic dermal wounds in patients at risk for the above listed problems.

The gel device can be used as part of any debridement procedure, used alone or as an adjuvant to a mechanical removal remedies (a specific brush, hand instrument or any kind of wound dressings. There are no incompatibilities of the product known, but concomitant use of vacuum devices should be avoided since it can remove the active gel from the wound surface.

Mixing the Gel:

The contents of the syringe must be completely injected into the vial containing the hydrogen peroxide.

Shake the vial to aid mixing, without removing the syringe.

Draw the mixture into the syringe, remove the vial and screw the tip tightly in the Luer-lock connection and use it directly to apply the gel in the area of interest.

The mixed gel must be used within 20 minutes. This is because the active hydrogen peroxide loses its efficacy after this time. The loss of activity does not pose any hazard to patient or environment as the peroxide and gel decomposes to water carbon dioxide and oxygen.

The recommended method of use for non-invasive treatment of chronic wounds is like this:

1. After removal of suppuration and excess wound fluid the gel is mixed and applied carefully onto the wound surface using the supplied applicator tip.
2. After application, let the gel sit for three to ten minutes to work, depending on the severity of the wound. Do not use any dressings or wipes during this time. The gel will chemically clean the area of interest.
3. After the cleaning time has ended, the gel should be removed with a humid wipe, removing as much as possible from the surface. Discard the wipe.
4. If necessary, repeat the procedure until the wound is visually clean.
5. When the wound debridement is satisfactory, cover the wound with a last application of the gel. Distribute evenly and let the gel set.
6. Cover the wound with the gel with a suitable wound dressing.
7. The gel and wound dressing should be left in place until the next scheduled wound debridement and/or change of wound dressing.
8. The patient can live as normal after the procedure. There are no extraordinary postoperative precautions when using the gel.

Example 17

In Vivo Compatibility to CaP Microparticles in Poloxamer Gel and $H_2O_2$

Test System

Species: Rabbit

Strain: New Zealand White

Experimental Design

Animals were identified as numbers 1 to 6 and allocated to dose group.

Administration of Test and Control Items

On the day before test item administration the hair was removed from an area of at least 8 cm×10 cm across the dorsal area of the trunk. On the following day, 4 gauze patches (2.5 cm×2.5 cm) was applied topically as in table 1:

TABLE 1

| Animal | Site | Treatment | Amount Applied (mL) |
|---|---|---|---|
| 1-6 | 1 | 3% H202 with 25% poloxamer Gel | 0.5 |
| | 2 | 4% H202 with 25% poloxamer Gel | 0.5 |
| | 3 | 5% H202 with 25% poloxamer Gel and 5 g/L OCP | 0.5 |
| | 4 | 25% poloxamer Gel | 0.5 |

Each patch was covered with micropore semi-occlusive tape and elastic bandage was wrapped round the torso of the animals.

The patches as removed 1, 24, 48, 72 and 96 hrs. and the test sites delineated. Test sites were wiped with gauze and room-temperature distilled water. To remove the last remnants of the poloxamer Gel, cold water (below 15° C.) was used.

Justification of Route and Dosage Levels

The dermal route of administration was selected for this study as this route has been defined as a possible route of human exposure, i.e. in wound care.

A dosage of 0.5 mL of each test item was selected for this study because it is routinely used in studies of this type.

Dermal Scoring

Frequency: 1, 24, 48, 72 and 96 h after patch removed.

Procedure: Skin was assessed for erythema and eschar formation, oedema formation, skin thickening, desquamation and any other reaction to the treatment.

CONCLUSIONS

There were no necropsy or histological findings attributed to the application of any of the test gels to intact rabbit skin after either 1 or 6 days after removal. The devices were deemed safe for testing in human dermal applications.

The invention claimed is:

1. An antimicrobial and/or anti-inflammatory composition for cleaning and/or debriding a biological surface and/or a biomaterial surface in situ, consisting of a. $H_2O_2$ at a final concentration of between 0.1-5% v/v, and b. a composite hydrogel formulation comprising poloxamers at a concentration of 10-40% w/v, wherein the ratio of the concentration of component a to component b in the composition is 1:10; and wherein the composition is liquid at a temperature of at the most 30° Celsius.

2. A kit comprising a composition according to claim 1, the kit further comprising h. at least two containers comprising said components a. and b., respectively, i. a syringe and a vial, j. a connector device, k. an applicator tip, and l. an instruction leaflet.

3. A kit according to claim 2, further comprising m. a mixing device and n. a debridement tool.

4. A kit comprising a composition according to claim 1, wherein said two components a. and b. are provided in a two-chamber syringe.

5. A process for removal of biofouling, biofilm and/or necrotic tissue from a biological surface and/or a biomaterial surface in situ comprising the step of applying a composition according to claim 1 to the surface.

6. A method for the treatment and/or prevention of periimplantitis, gingivitis, mucositis, peri-implant mucositis, periodontitis, and/or chronic and/or infected dermal ulcers comprising the step of applying a composition according to claim 1 to the tissue to be treated.

7. An antimicrobial and/or anti-inflammatory composition for cleaning and/or debriding a biological surface and/or a biomaterial surface in situ, consisting of a. $H_2O_2$ at a final concentration of between 0.1-5% v/v, and b. a composite hydrogel formulation comprising poloxamers at a concentration of 10-40% w/v, and c. microparticles having a mean particle diameter (D50) of 20-200 μm, wherein said microparticles are organic or inorganic;

wherein the ratio of the concentration of component a to component b in the composition is 1:10; and wherein the composition is liquid at a temperature of at the most 30° Celsius.

* * * * *